United States Patent [19]
Kool

[11] Patent Number: 5,808,036
[45] Date of Patent: Sep. 15, 1998

[54] STEM-LOOP OLIGONUCLEOTIDES CONTAINING PARALLEL AND ANTIPARALLEL BINDING DOMAINS

[75] Inventor: Eric T. Kool, Rochester, N.Y.

[73] Assignee: Research Corporation Technologies Inc., Tucson, Ariz.

[21] Appl. No.: 466,670

[22] Filed: Jun. 6, 1995

Related U.S. Application Data

[62] Division of Ser. No. 115,497, Sep. 1, 1993, Pat. No. 5,514,546.

[51] Int. Cl.$^6$ .......................... C07H 21/02; C07H 21/04; C12N 5/10
[52] U.S. Cl. .......................... 536/24.3; 435/6; 435/320.1; 435/325; 435/375; 536/23.1; 536/24.5
[58] Field of Search .............................. 435/6, 69.1, 91.4, 435/172.1, 320.1, 240.1, 243, 252.3, 254.11, 325, 375; 514/44; 536/23.1, 24.1, 24.3, 24.31, 24.32, 24.5

[56] References Cited

U.S. PATENT DOCUMENTS

| | | | |
|---|---|---|---|
| 4,868,103 | 9/1989 | Stavrianopoulous et al. | 435/5 |
| 5,208,149 | 5/1993 | Inouye | 435/172.3 |
| 5,422,251 | 6/1995 | Fresco | 435/91.1 |
| 5,585,479 | 12/1996 | Hoke et al. | 536/24.5 |

OTHER PUBLICATIONS

Baumann et al. (1988) Interaction of DNA Hairpin Loops and a Complementary Strand by a Triplet of Base Pairs. *Biochem. Biophys. Res. Commun.* 157:986–991.
D'Souza et al. (1992) Strong Binding of Single–Stranded DNA by Stem–Loop Oligonucleotides. *J. Biomolec. Struc. & Dyam.* 10:141–152.
Durand et al. (1992) Triple–Helix Formation by an Oligonucleotide Containing One $(dA)_{12}$ and Two $(dT)_{12}$ Sequences Bridged by Two Hexaethylene Glycol Chains. *Biochemistry* 31:9197–9204.
Ecker et al. (1992) Pseudo–Half–Knot Formation with RNA. *Science* 257:958–961.
Kool (1991) Molecular Recognition by Circular Oligonucleotides: Increasing the Selectivity of DNA Binding. *J. Amer. Chem. Soc.* 113: 6265–6266.
Giovannangeli et al. (1991) Single–Stranded DNA as a Target for Triple–Helix Formation. *J. Am. Chem. Soc.* 113:7775–7777.
Manzini et al. (1990) Triple Helix Formation by Oligopurine–Oligopyrimidine DNA Fragments. *J. Mol. Biol.* 213:833–843.
Prakash et al. (1992) Structural Effects in the Recognition of DNA by Circular Oligonucleotides. *J. Amer. Chem. Soc.* 114: 3523–3527.
Prakash et al. (Apr. 5–10, 1992) Recognition of DNA and RNA by Circular Oligonucleotides: Strong Binding and High Selectivity. American Chemical Society 203rd National Meeting, abstract ORGN473.

(List continued on next page.)

*Primary Examiner*—Nancy Degen
*Assistant Examiner*—Thomas G. Larson
*Attorney, Agent, or Firm*—Scully, Scott, Presser & Murphy

[57] ABSTRACT

The present invention provides stem-loop oligonucleotides containing a double-stranded stem domain of at least about 2 base pairs and a single-stranded loop domain. The loop domains of the present oligonucleotides include at least one parallel binding (P) domain separated by at least about 3 nucleotides from a corresponding anti-parallel binding (AP) domain. Each P and corresponding AP domain of the present oligonucleotides can bind detectably to one strand of a defined nucleic acid target wherein the P domain binds in a parallel manner to the target and the corresponding AP domain binds in an anti-parallel manner to the target. The present stem-loop oligonucleotides can bind to both single-stranded and double-stranded target nucleic acids. The present invention also provides methods of using these oligonucleotides as well as kits and pharmaceutical compositions containing these oligonucleotides.

27 Claims, 8 Drawing Sheets

OTHER PUBLICATIONS

Prakash et al. (Apr. 5–10, 1992) Structural Effects in the Recognition of Single–Stranded DNA by Circular Oligonucleotides. American Chemical Society 203rd National Meeting, abstract ORGN341.

Prakash et al. (1991) Molecular Recognition by Circular Oligonucleotides: Strong Binding of Single–Stranded DNA and RNA. *J. Chem. Soc. Chem. Commun.* 113:1161–1163.

Rumney IV et al. (Aug. 23, 1992) DNA Recognition by Hybrid Oligoether–Oligonucleotide Macrocycles. American Chemical Society 204th National Meeting, abstract ORGN394.

Voloshin et al. (1988) Chemical Probing of Homopurine–Homopyrimidine Mirror Repeats in Supercoiled DNA. *Nature* 333:475–476.

Xodo et al. (1990) Spectroscopic and Calorimetric Investigation on the DNA Triplex Formed by d(CTCT-TCTTTCTTTTCTTTCTTCTC) and d(GAGAAGAAAGA) at acidic pH. *Nucleic Acids Res.* 18:3557–3564.

D'Souza et al. Medline Abstract with Publication Date for J. Biomol. Structure and Dynamics 10(1): 141–152, Aug. 1992.

Goodchild Bioconjugate Chem. 1(3): 165–167, 1990.

Gura Science 270:575–577, Aug. 1995.

Uhlmann et al. Chem. Rev. 90(4): 543–584, Jun. 1990.

Gewirtz et al. "Facilitating oligonucleotide delivery: Helping antisense deliver on its promise" Proc. Natl. Acad. Sci. USA 93: 3161–3163, Apr. 1996.

Miligan et al. "Current concepts in antisense drug design" J. Med. Chem. 36: 1923–1937, Jul. 1993.

Stull et al. "Antigene, ribozyme, and aptamer nucleic acid drugs; Progress and prospects" Pharm. Res. 12: 465–483, Apr. 1995.

Webster's II New Riverside Dictionary, Houghton Mifflin Co, Boston, p. 407, 1994.

STEM-LOOP OLIGONUCLEOTIDES CONTAINING PARALLEL AND ANTIPARALLEL BINDING DOMAINS

This is a divisional of application Ser. No. 08/115,497, filed on Sep. 1, 1993, now U.S. Pat. No. 5,514,546.

This invention was made with United States Government support under Grant No. N00014-92-J-1740 awarded by the Office of Naval Research; Grant Nos. GM-46625 and RR-00769 awarded by National Institute of Health; and Grant No. IRG-18-34 awarded by the American Cancer Society (ACS).

FIELD OF THE INVENTION

The present invention provides stem-loop oligonucleotides capable of strong binding to a target DNA or RNA. Moreover, stem-loop oligonucleotides are resistant to nucleases and bind to a target with high selectivity and affinity. Such strong binding allows the present stem-loop oligonucleotides to be utilized in a variety of ways. For example, stem-loop oligonucleotides can be labeled for use as probes to detect or isolate a target nucleic acid. Stem-loop oligonucleotides can also be transcribed within, or administered to, a cell to provide in vivo regulators of DNA replication, RNA transcription, protein translation, reverse transcription, and other processes involving nucleic acid templates.

BACKGROUND OF THE INVENTION

An oligonucleotide binds to a target nucleic acid by forming hydrogen bonds between bases in the target and the oligonucleotide. Common B DNA has conventional adenine-thymine (A-T) and guanine-cytosine (G-C) Watson and Crick base pairs with two and three hydrogen bonds, respectively. Conventional hybridization technology is based upon the capability of sequence-specific DNA or RNA probes to bind to a complementary target nucleic acid via Watson-Crick hydrogen bonds. However, other types of internucleotide hydrogen bonding patterns are known wherein atoms not involved in Watson-Crick base pairing to a first nucleotide can form hydrogen bonds to another nucleotide. For example, thymine (T) can bind to an AT Watson-Crick base pair via hydrogen bonds to the adenine, thereby forming a T-AT base triad. Hoogsteen (1959, *Acta Crystallographica* 12:822) first described the alternate hydrogen bonds present in T-AT and C-GC base triads. More recently, G-TA base triads, wherein guanine can hydrogen bond with a central thymine, have been observed (Griffin et al., 1989, *Science* 245:967–971).

Oligonucleotides which can bind to a target with both Watson-Crick and non-Watson-Crick hydrogen bonds form extremely stable complexes which have a variety of in vivo and in vitro utilities. To date there has been no disclosure of a stem-loop oligonucleotide with the necessary structural features to achieve stable target binding via Watson-Crick and alternate hydrogen bonds.

Oligonucleotides have been used for a variety of utilities. For example, oligonucleotides can be used as probes for target nucleic acids that are immobilized onto a filter or membrane, or are present in tissues, e.g. as described in Sambrook et al. (1989, *Molecular Cloning: A Laboratory Manual,* Vols. 1–3, Cold Spring Harbor Press, NY). However, the utility of linear oligonucleotide probes is frequently limited by their poor binding stability and selectivity.

Furthermore, there has been great interest recently in developing oligonucleotides as regulators of cellular nucleic acid biological function. This interest arises from observations on naturally occurring complementary, or antisense, RNA used by some cells to control protein expression. However, the development of oligonucleotides for in vivo regulation of biological processes has been hampered by several long-standing problems, including the low binding affinity and nuclease sensitivity of linear oligonucleotides.

For example, transcription of the human c-myc gene has been inhibited in a cell free, in vitro assay system by a 27-base linear oligonucleotide designed to bind to the c-myc promoter (Cooney et al., 1988, *Science* 241:456). Inhibition was only observed using a carefully controlled in vitro assay system wherein lower than physiological temperatures were employed, and many cellular enzymes had been removed or inactivated. These conditions were necessary because linear oligonucleotides bind with low affinity and are highly susceptible to enzymes which degrade linear pieces of DNA.

Splicing of a pre-mRNA transcript essential for Herpes Simplex virus replication has also been inhibited with a linear oligonucleotide which was complementary to an acceptor splice junction. In this instance, a methylphosphonate linkage was employed in the linear oligonucleotide to increase its nuclease resistance. Addition of this chemically-modified oligonucleotide to the growth medium caused reduction in protein synthesis and growth of uninfected cells, most likely because of toxicity problems occurring at high oligonucleotide concentrations (Smith et al., 1986, *Proc. Natl. Acad. Sci. USA* 83:2787–2791).

In another example, linear oligonucleotides were used to inhibit human immunodeficiency virus replication in cultured cells. Linear oligonucleotides complementary to sites within or near the terminal repeats of the retrovirus genome and within sites complementary to certain splice junctions were most effective in blocking viral replication. However, these experiments required large amounts of the linear oligonucleotides before an effect was obtained, presumably because of the low binding affinity and vulnerability of these linear oligonucleotides to nucleases (Goodchild et al., 1988, *Proc. Natl. Acad. Sci. USA* 85:5507–5511).

Linear oligonucleotides have been observed to bind by non-Watson-Crick or Watson-Crick hydrogen bonding in vitro. However, linear oligonucleotides which are bound to target via only non-Watson-Crick or only Watson-Crick hydrogen bonds are not very stable, and can be readily displaced from the target under normal cellular conditions.

Xodo et al. (1990, *Nucleic Acids Res.* 18:3557–3564) and Giovannangeli et al. (1991, *J. Am. Chem. Soc.* 113:7775–7777) disclose linear pyrimidine oligonucleotides in which one domain of the oligonucleotide reportedly forms an antiparallel duplex with a target purine sequence, and a second domain "folds back" and binds to the duplex, thus forming a bimolecular triple helix. The resulting "U-shaped" oligonucleotides of Xodo et al. and Giovannangeli et al. thus apparently bind the target with both Watson-Crick and non-Watson-Crick bonds. However, it has been found in accordance with the present invention that such linear oligonucleotides do not bind with optimal affinity.

Baumann et al. (1988, *Biochem. Biophys. Res. Commun.* 157:986–991) disclose stem-loop oligonucleotides wherein the loop can intermolecularly bind to a single stranded oligomer by Watson-Crick base pairing only. This interaction appears to mimic the native interaction that occurs between the tRNA anticodon loop and the mRNA codon.

Single-stranded circles of DNA or RNA are known which can bind to target via both Watson-Crick and non-Watson-Crick hydrogen bonding (Kool, 1991, *J. Amer. Chem. Soc.*

113:6265–6266; and Prakash et al., 1991, *J. Chem. Soc. Chem. Commun.* 113:1161–1163). However, Kool and Prakash et al. are particularly drawn to circular oligonucleotides and do not disclose or teach stem-loop oligonucleotides.

Moreover, such circular oligonucleotides are not always ideal for in vivo regulation of biosynthetic processes. For example, such circular oligonucleotides can be made only in vitro. In contrast, the present invention provides stem-loop oligonucleotides which are easily synthesized by recombinant technology in vivo. Furthermore, the in vitro synthesis of circular oligonucleotides can be expensive and time-consuming relative to the easily synthesized oligonucleotides of the present invention.

The present invention provides stem-loop oligonucleotides which have many of the desirable attributes of circular oligonucleotides, e.g. nuclease resistance (Tang et al., 1993, *Nucleic Acids Res.* 21:2729–2735). However the present stem-loop oligonucleotides are much simpler to make both in vivo and in vitro. Moreover, the present stem-loop oligonucleotides bind target via both Watson-Crick and non-Watson-Crick hydrogen bonding. The present stem-loop oligonucleotides bind with strong affinity and high selectivity to their targeted nucleic acids.

SUMMARY OF THE INVENTION

The present invention is directed to stem-loop oligonucleotides including a double-stranded stem domain of at least about 2 base pairs and a single-stranded loop domain. The loop domain has at least one parallel binding (P) domain which is separated by at least about 3 nucleotides from a corresponding anti-parallel binding (AP) domain. According to the present invention each P and corresponding AP domain can simultaneously and detectably bind to one strand of a defined nucleic acid target. However, the P domain binds in a parallel manner to the target while the corresponding AP domain binds in an anti-parallel manner to the target. In one embodiment the target has a known nucleotide sequence from which at least 5 nucleotide positions in the P domain and in the corresponding AP domain are determined according to the rules provided by the present invention. Moreover the two strands of the stem can be covalently cross-linked. The present stem-loop oligonucleotides can be expressed within or taken up by a cell.

The present invention also provides a kit for detection, diagnosis or isolation of a target or template nucleic acid. Such a kit has at least one first container providing a stem-loop oligonucleotide of the present invention wherein at least one P domain and corresponding AP domain of the oligonucleotide can selectively bind to the target or template nucleic acid.

The present invention is further directed to a complex formed between any of the present oligonucleotides and a target nucleic acid.

In another embodiment the present invention provides an expression vector including a sequence encoding any one of the present oligonucleotides operably linked to segment of the vector which effects expression of an RNA copy of the oligonucleotide. Host cells containing such an expression vector are also provided.

The present invention further contemplates a method for regulating biosynthesis of a DNA, an RNA or a protein in a mammalian cell which includes expressing an RNA copy of at least one of the present oligonucleotides from an expression vector present in the mammalian cell. According to the present invention, such expression of an RNA copy regulates biosynthesis of the DNA, the RNA or the protein, by binding of the RNA copy to a target contained within a nucleic acid template for the DNA, the RNA or the protein.

In another embodiment the present invention provides a method of regulating biosynthesis of a DNA, an RNA or a protein which includes contacting a nucleic acid template for the DNA, the RNA or the protein with at least one of the present oligonucleotides. As provided herein the oligonucleotide binds to a target sequence contained within the template under physiological conditions and thereby regulates biosynthesis of the DNA, the RNA or the protein. RNA stem-loop oligonucleotides are preferred for binding to RNA targets; DNA or RNA stem-loop oligonucleotides, and especially DNA stem-loop oligonucleotides, are preferred for binding to DNA targets.

Moreover the present invention provides a method for selectively regulating the biosynthesis of a DNA, an RNA or a protein in a mammalian tumor cell, e.g. in vivo, without substantially altering such biosynthesis in a non-tumor cell. This method includes administering to the mammal an oligonucleotide of the present invention which has at least two pairs of P and corresponding AP binding domains. The first target bound by the first pair of binding domains is a guanine-rich target present within a template nucleic acid for the DNA, the RNA or the protein, and the second target bound by a second pair of binding domains is a guanine-poor target which is not present within the targeted template. Since formation of C-GC triads is favored at low pH and tumor cells have a substantially lower pH than normal cells, the oligonucleotide will bind to the template in the tumor cells but will not bind to such a template in the normal cells.

In a related embodiment the present invention provides a method for selectively binding a guanine-rich target to a cytosine-rich pair of binding domains in an oligonucleotide. In this embodiment the oligonucleotide has a second pair of cytosine-poor binding domains, and a guanine-poor target is also present. This method includes contacting the guanine-rich target and the guanine-poor target with the oligonucleotide at a pH of about 5.0 to about 6.8. The conditions utilized for this method are also sufficient for nucleic acid hybridization.

The present invention further provides a method of strand displacement in a double-stranded nucleic acid target which includes contacting the target with a stem-loop oligonucleotide of the present invention for a time and under conditions effective to denature the target and to bind the stem-loop oligonucleotide to a single strand of the target.

In another embodiment the present invention provides a method of specific cell type drug delivery which includes administering an oligonucleotide of the present invention to an animal wherein the oligonucleotide has a covalently linked drug.

In a still further embodiment the present invention provides a method of detecting a target nucleic acid which includes providing a sample to be assayed for the target nucleic acid with a stem-loop oligonucleotide of the present invention. After the sample and the oligonucleotide are in contact for a time and under conditions sufficient to form an oligonucleotide-target complex, the complex is detected.

The present invention also provides pharmaceutical compositions containing a pharmaceutically effective amount of at least one of the oligonucleotides of the present invention and a pharmaceutically acceptable carrier. In one embodiment, such compositions contain a biosynthesis-regulating amount of the oligonucleotide and are useful for regulating biosynthesis of a nucleic acid or protein.

BRIEF DESCRIPTIONS OF THE DRAWINGS

FIG. 1 depicts the formation of a stem-loop oligonucleotide:target complex. The target (T) and the parallel (P), and antiparallel (AP) and stem domains of the stem-loop oligonucleotide are indicated. The 5' to 3' orientation of each strand is indicated.

Figure 3:
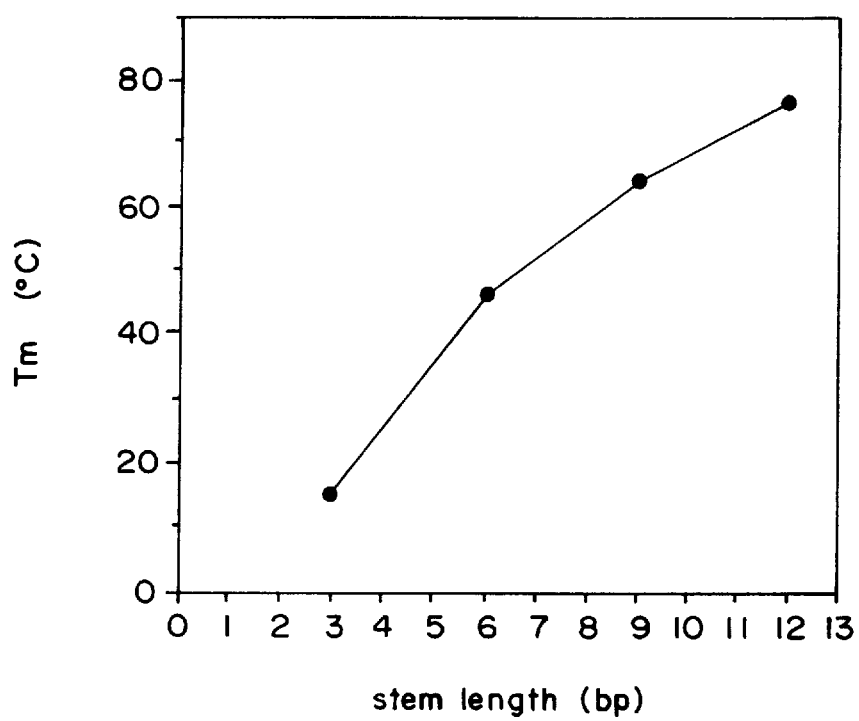
FIG. 3 depicts the intramolecular melting temperatures ($T_m$) of stem-loop oligonucleotides having varying stem lengths. The measured $T_m$'s rise with increasing stem length from 15° C. for the 3-base stem to 75° C. for the twelve-base stem.
Figure 4:
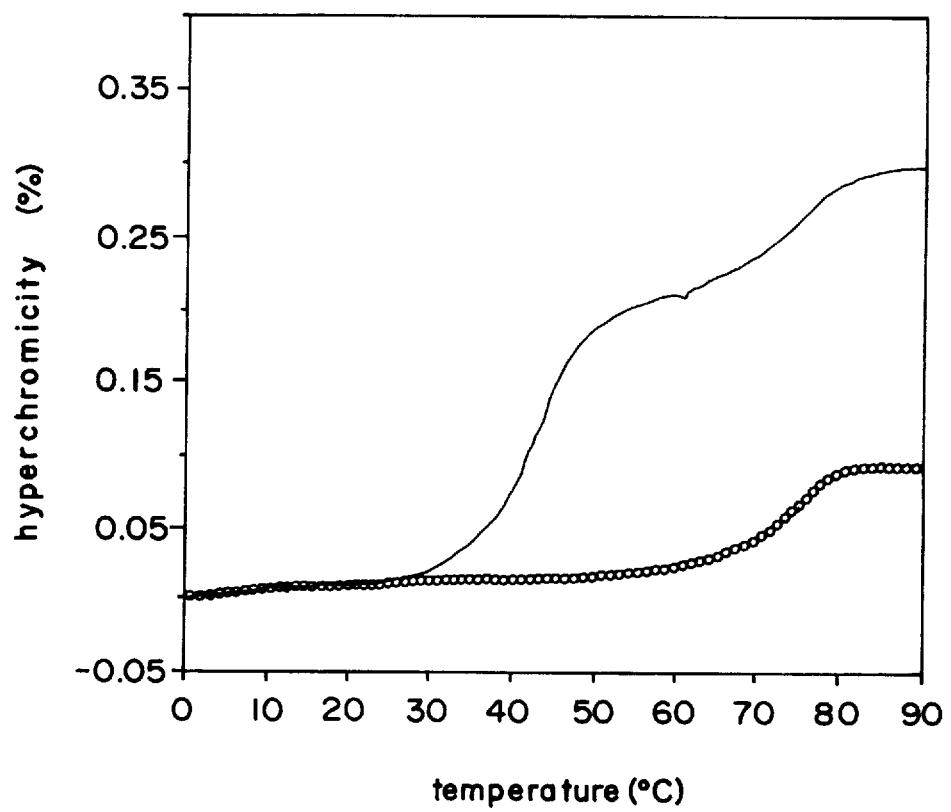

FIG. 4 depicts the percent hyperchromicity vs. temperature of a SEQ ID NO:5 stem-loop oligonucleotide in the presence (solid line) and absence (open circles) of a SEQ ID NO:6 target. In the absence of target a single melting transition occurs at about 75° C. which, as illustrated in FIG. 3, corresponds to the melting of the SEQ ID NO:5 stem. However, in the presence of target two melting transitions occur, one at about 45° C. and one at about 75° C. These melting curves indicate that melting of both the SEQ ID NO:5 P and AP domains from target occurs simultaneously at about 45° C.

Figure 5:
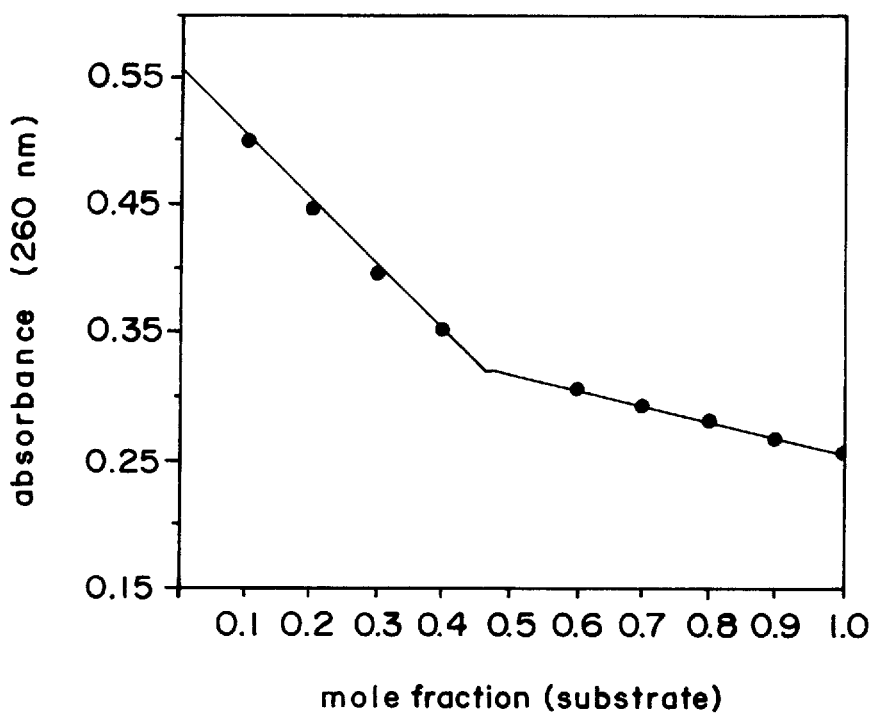

FIG. 5 depicts the absorbance of a mixture containing varying mole fractions of the SEQ ID NO:6 target (i.e. substrate) mixed with the SEQ ID NO:2 stem-loop oligonucleotide. The inflection point of the observed absorbance provides the mole fraction of SEQ ID NO:6 target needed for complete complexation with the stem-loop oligonucleotide.

Figure 6:
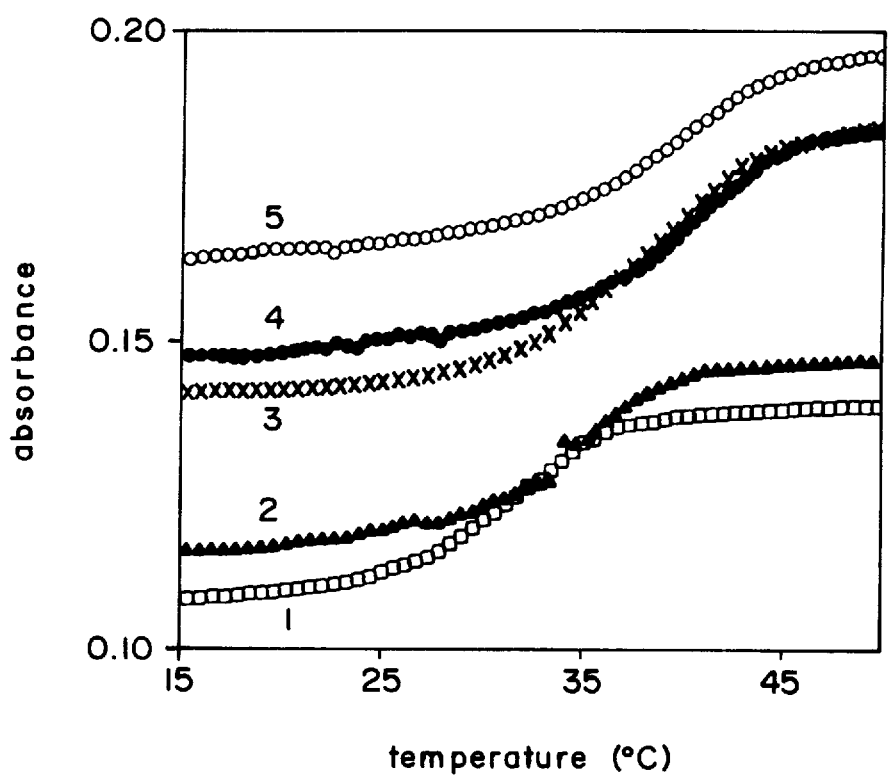

FIG. 6 depicts melting curves for intermolecular complexes formed between the SEQ ID NO:1–5 stem-loop oligonucleotides and the SEQ ID NO:6 target. The melting curves of complexes formed with the SEQ ID NO:1 (□), SEQ ID NO:2 (▲), SEQ ID NO:3 (X), SEQ ID NO:4 (●) and SEQ ID NO:5 (○) stem-loop oligonucleotides are depicted.

Figure 7:
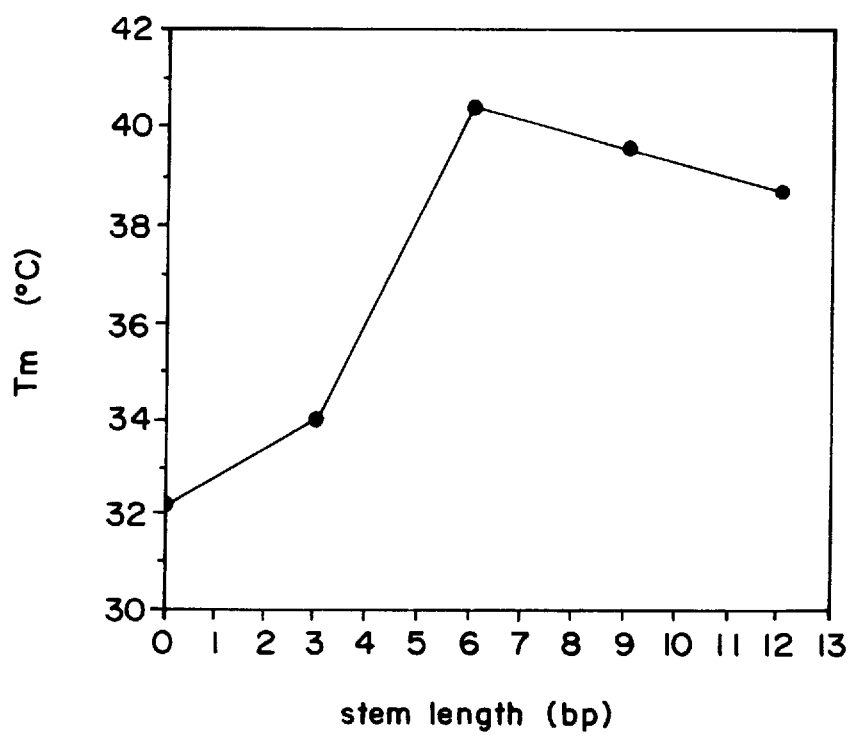

FIG. 7 depicts the effect of stem length on the melting temperature of the target from stem-loop oligonucleotides.

DETAILED DESCRIPTION OF THE INVENTION

The present invention relates to stem-loop oligonucleotides which can bind to nucleic acid targets with high affinity and selectivity. Such strong, selective binding of these oligonucleotides to either single- or double-stranded DNA or RNA targets provides a variety of uses, including methods of regulating such biological processes as DNA replication, RNA transcription, RNA splicing and processing and protein translation. Similarly, the strong binding properties of these stem-loop oligonucleotides makes these oligonucleotides ideal diagnostic probes or markers to localize, for example, specific sites in a chromosome or other DNA or RNA molecules. Additionally, the present stem-loop oligonucleotides are useful for isolation of complementary nucleic acids or for sequence-specific delivery of drugs or other molecules into cells.

The stem-loop structure, also known as a hairpin, is a structural motif of nucleic acids which is known to occur in natural sequences of DNA and RNA. Stem-loops arise from complementarity within a single-stranded nucleic acid whereby a single strand folds back upon itself to form a double-stranded stem and a single-stranded loop (see, e.g. Haasnoot et al., 1986, *Journal of Biomolecular Structure and Dynamics*, 3:843).

The stem-loop oligonucleotides of the present invention have a double-stranded stem domain of at least about 2 base pairs and a single-stranded loop domain having at least one parallel binding (P) domain and a corresponding antiparallel binding (AP) domain. The P and corresponding AP binding domains are separated by at least about 3 nucleotides. Each P and corresponding AP domain is capable of binding detectably to one strand of a defined nucleic acid target wherein the P domain binds in a parallel manner to the target and the corresponding AP domain binds in an antiparallel manner to the target. Accordingly, each P and AP domain exhibits sufficient complementarity to detectably bind to the nucleic acid target. Detectable binding as defined herein refers to binding of the stem-loop oligonucleotide to a target sequence which can be qualitatively or quantitatively observed by methods known to the ordinarily skilled artisan. Such methods include, for example, a change in light absorption or fluorescence, stable localization of a reporter molecule at a target site, and other physical and functional methods described in detail hereinbelow.

As used herein, binding of nucleic acids in a parallel manner means that the 5' to 3' orientation is the same for two bound strands of nucleotides in a complex. This is the type of binding present between he target strand and the P domain. As used herein, binding of nucleic acids in an anti-parallel manner means that the 5' to 3' orientations of two strands or nucleotides in a complex are aligned in opposite directions, i.e. the strands are aligned as in the typical Watson-Crick base pairing arrangement of double helical DNA.

Figure 1:
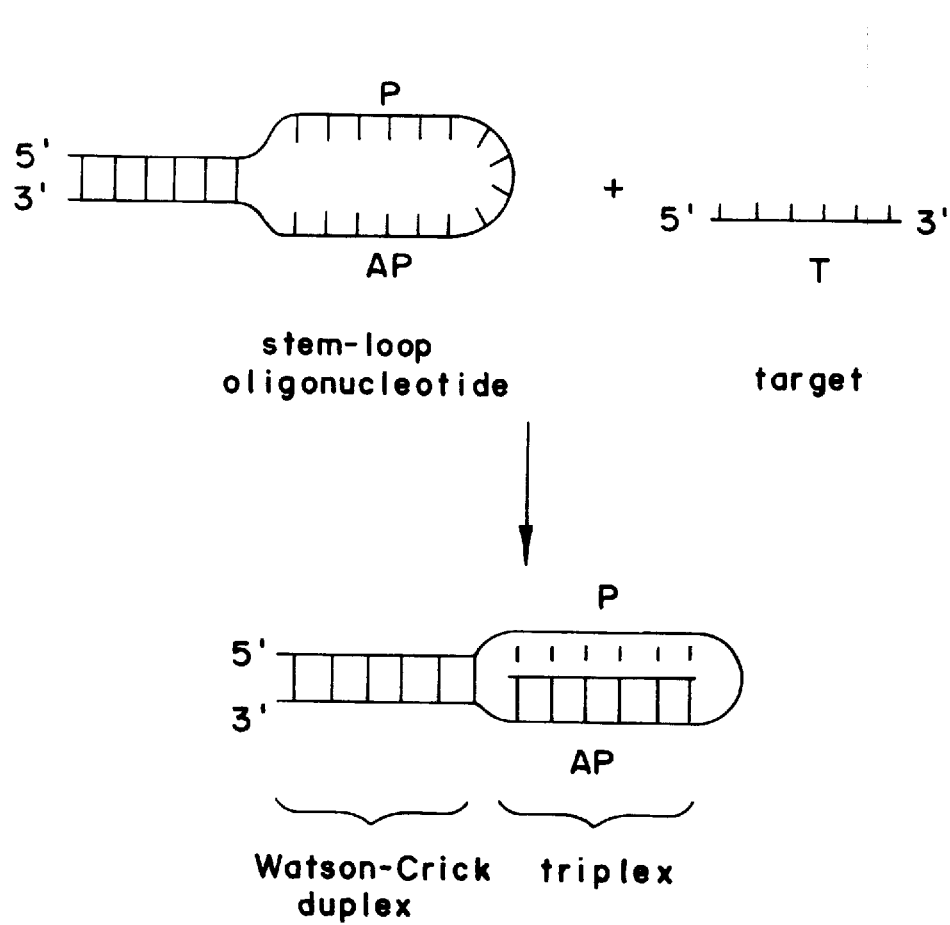

A schematic diagram is set forth in FIG. 1 to illustrate one embodiment of the structure of the present stem-loop oligonucleotide domains relative to a target nucleic acid strand. As illustrated in FIG. 1, the stem of the oligonucleotide is formed by base-pairing of complementary bases in the 5' and 3' ends of the oligonucleotide. The present invention also encompasses stem-loop oligonucleotides in which, for example, the AP domain is at the 5' end of the oligonucleotide and the P domain is at the 3' end.

The stem domains of the present stem-loop oligonucleotides are at least about 2 base pairs in length. A preferred length is about 3 base pairs and an especially preferred length is about 6 base pairs. The stem is preferably kept as short as possible without adversely affecting the stability of the stem-loop structure. Such short stems are less likely to cause steric hindrance of oligonucleotide binding to target. The stem can further comprise an overhanging single-stranded region, i.e., the stem is a partial duplex. In a preferred embodiment the overhang is closer to the AP domain than to the P domain when the oligonucleotide is viewed linearly. The preferred length of the single-stranded overhang is from about 3 to about 10 nucleotides.

The two strands of the stem can be covalently cross-linked such that the stability of the stem structure is no longer dependent upon stem length. Therefore the stem length need only be long enough to permit cross-linking, i.e. only about 2 base pairs. Cross-linking is done by procedures readily available to the skilled artisan, e.g. as described in Calabresi et al. (1980, in Gilman et al. eds. *The Pharmacological Basis of Therapeutics*, MacMillan Publishing Co., Inc., pp.1256–1272) and Glick et al. (1992, *J. Am. Chem. Soc.* 114:5447–8).

Each P, AP and target domain can independently have about 2 to about 200 nucleotides with preferred lengths being about 4 to about 100 nucleotides. The most preferred lengths are 6 to 20 nucleotides.

The loop of the oligonucleotide comprises at least one pair of P and corresponding AP binding domains separated by at least about 3 nucleotides. The loop domains which separate the P and AP domains can independently have from about 3 to about 2000 nucleotides. A preferred separation length is from about 4 to about 8 nucleotides with an especially preferred length being about 5 nucleotides. The stem domain can be considered to contribute two nucleotides to a loop domain separating a P and corresponding AP domain (i.e., the "width" of the stem is two nucleotides). In other words, the approximate 3 nucleotide separation distance between the P and AP domains can include two nucleotides at the neck of the stem and one or more loop domain nucleotides. In another embodiment, the loop domain between the P and AP domains can comprise only the two nucleotides which form the width of the stem.

When more than one P and AP binding domain is present, such binding domains can be separated from other P and AP domains by portions of the loop domain whose lengths can be sufficient to permit binding to multiple targets. When a stem-loop oligonucleotide of the present invention includes, e.g., two pairs of corresponding binding domains, these pairs of corresponding binding domains can bind to separate target sites, or to the same target site under different conditions.

In accordance with this invention, the nucleotide sequences of the P and AP domains are determined from the defined sequence of the nucleic acid target by reference to the base pairing rules provided hereinbelow. A target can be RNA or DNA and either single- or double-stranded. A target is selected by its known functional and structural characteristics. For example, a target can be selected by its capability for detection or isolation of a nucleic acid, e.g. a template for biosynthesis of a DNA, an RNA or a protein. Some preferred targets are coding regions, origins of replication, reverse transcriptase binding sites, transcription regulatory elements, RNA splicing junctions, or ribosome binding sites, among others. Preferred targets are generally rich in purines, i.e. adenines and guanines.

Unlike linear oligonucleotides, the present stem-loop oligonucleotides can displace one strand of a double-stranded target under conditions where denaturation of the double-stranded target is thermodynamically unfavorable. Linear oligonucleotides do not have this capacity to displace a strand of a duplex. For example, the half-life of a double-stranded target in the presence of a complementary linear oligonucleotide is about 58 min, i.e. so long that the linear oligonucleotide has little utility for displacing one strand of the duplex target. However, a double-stranded target can have a half-life of only about 30 seconds in the presence of the present stem-loop oligonucleotides. Therefore, the stem-loop oligonucleotides of the present invention have utility not only for binding single-stranded targets, but also for binding to double-stranded targets. Accordingly, since both single- and double-stranded nucleic acids are available as targets for the present stem-loop oligonucleotides, these stem-loop oligonucleotides have greater utility than linear oligonucleotides. For example, the present stem-loop oligonucleotides are better regulators of biological processes in vivo and better in vitro diagnostic probes than corresponding linear oligonucleotides.

The nucleotide sequence of the target DNA or RNA can be known in full or in part. When the target nucleotide sequence is completely known, the sequences of the P and AP domains are designed with the necessary degree of complementarity to achieve detectable binding. Such binding can be detected by known procedures, for example by a change in light absorption or fluorescence or by observing whether a reporter molecule, linked to a stem-loop oligonucleotide probe, can be stably localized at a target site.

In some instances, the target sequence can be represented by a consensus sequence or be only partially known. For example, stem-loop oligonucleotides which bind to an entire class of targets represented by a consensus sequence can be obtained by designing the P and AP domains from the target consensus sequence. In this instance some of the targets may match the consensus sequence exactly and others may have a few mismatched bases. The present oligonucleotides can bind to fully complementary and partially mismatched targets. Accordingly, if a portion of a target sequence is known, one skilled in the art can refer to the base pairing rules provided hereinbelow to design stem-loop oligonucleotides which bind to that target with higher affinity than a linear oligonucleotide of similar sequence.

Thus, the present invention is also directed to stem-loop oligonucleotides having P and AP domains which are sufficiently complementary to bind to a nucleic acid target wherein a sufficient number, but not necessarily all, nucleotide positions in the P and AP domains are determined from the target sequence in accordance with the base pairing rules of this invention. The number of determined (i.e. known) positions is that number of positions which are necessary to provide sufficient complementarity for binding of the subject oligonucleotides to their targets, as detected by standard procedures including a change in light absorption upon binding or melting.

The base pairing rules of the present invention provide for the P domain to bind to the target by forming base pairs wherein the P domain and target nucleotides have the same 5' to 3' orientation. In particular, these rules are satisfied to the extent needed to achieve binding of a stem-loop oligonucleotide to its nucleic acid target, i.e. the degree of complementarity need not be 100% so long as binding can be detected. Hence, the general rules for determining the sequence of the P domain are thus:

when a base for a position in the target is guanine or a guanine analog, then P has cytosine, or a suitable analog thereof, in a corresponding position;

when a base for a position in the target is adenine, or an adenine analog then P has thymine or uracil, or suitable analogs thereof, in a corresponding position;

when a base for a position in the target is thymine, or a thymine analog, then P has cytosine or guanine, or suitable analogs thereof, in a corresponding position;

when a base for a position in the target is cytosine, or a cytosine analog, then P has cytosine, thymine or uracil, or suitable analogs thereof, in a corresponding position; and when a base for a position in the target is uracil, or a uracil analog, then P has cytosine, guanine, thymine, or uracil, or suitable analogs thereof, in a corresponding position.

The base pairing rules of the present invention provide for the AP domain to bind to the target by forming base pairs wherein the AP domain and target nucleotides are oriented in opposite directions. In particular these rules are satisfied to the extent necessary to achieve detectable binding of a stem-loop oligonucleotide to its nucleic acid target, i.e. the degree of complementarity can be less than 100%. Hence, the base pairing rules can be adhered to only insofar as is necessary to achieve sufficient complementarity for binding to be detected between the stem-loop oligonucleotide and its target.

Thus, the general rules for determining the sequence of the AP domain are as follows:

when a base for a position in the target is guanine, or a guanine analog, then AP has cytosine or uracil or thymine, or suitable analogs thereof, in a corresponding position;

when a base for a position in the target is adenine, or an adenine analog, then AP has thymine or uracil, or suitable analogs thereof, in a corresponding position;

when a base for a position in the target is thymine, or a thymine analog, then AP has adenine, or a suitable analog thereof, in a corresponding position; and when a base for a position in the target is cytosine, or a cytosine analog, then AP has a guanine, or a suitable analog thereof, in corresponding position;

when a base for a position in the target is uracil, or a uracil analog, then AP has adenine or guanine, or suitable analogs thereof, in a corresponding position.

In a preferred embodiment, the P, AP and loop domains are not complementary to each other.

Table 1 summarizes which nucleotides can form antiparallel base pairs or parallel base pairs with a defined target nucleotide.

TABLE 1

| Target Nucleotide[a] | Anti-Parallel Domain Nucleotide[a] | Parallel Domain Nucleotide[a] |
|---|---|---|
| G | C or U or T | C |
| A | T or U | T or U |
| T | A | C or G |
| C | G | C, T or U |
| U | A or G | C, G, T or U |

[a]Or a suitable analog

Two complementary single-stranded nucleic acids form a stable double helix (duplex) when the strands bind, or hybridize, to each other in the typical Watson-Crick fashion, i.e. via anti-parallel GC and AT base pairs. For the present invention, stable duplex formation and stable triplex formation is achieved when the P and AP domains exhibit sufficient complementarity to the target sequence to achieve stable binding between the stem-loop oligonucleotide and the target molecule. Stable binding occurs when an oligonucleotide remains bound to target under the conditions selected for detection.

According to the present invention, the complex formed between a stem-loop oligonucleotide and a target can include some base pairs and does not have to include only base triads. Therefore, some of the nucleotides of the P and AP domains can remain unbound to the target. Preferably, a sufficient number of base triads form to confer increased target binding stability for the present stem-loop oligonucleotides relative to a linear oligonucleotide which is 100% complementary to the target.

Moreover, when the target is contained in a nucleic acid template which extends beyond a central triple-stranded complex of the present invention, a P or an AP domain may bind as duplex on either side of the triple standard complex. Hence a target:stem-loop oligonucleotide complex can be partially two stranded and partially three-stranded, wherein two-stranded portions can be P:target duplexes, without bound AP nucleotides, or AP:target duplexes, without bound P nucleotides. This binding arrangement is referred to herein as a staggered binding arrangement.

Complementarity between nucleic acids is the degree to which the bases in one nucleic acid strand can hydrogen bond, or base pair, with the bases in a second nucleic acid strand. Hence, complementarity can sometimes be conveniently described by the percentage, i.e. proportion, of nucleotides which form base pairs between two strands or within a specific region or domain of two strands. For the present invention sufficient complementarity means that a sufficient number of base pairs exist between a target nucleic acid and the P and/or AP domains of the stem-loop oligonucleotide to achieve detectable binding. Moreover, the degree of complementarity between the P domain and the target and the AP domain and the target need not be the same. When expressed or measured by percentage of base pairs formed, the degree of complementarity can range from as little as about 30–40% complementarity to full, i.e. 100%, complementarity. In general, the overall degree of complementarity between the P or AP domain and the target is preferably at least about 50%. However, the P domain can sometimes have less complementarity with the target than the AP domain has with the target, for example the P domain can have about 30% complementarity with the target while the AP domain can have substantially more complementarity, e.g. 50% to 100% complementarity.

The degree of complementarity that provides detectable binding between the subject stem-loop oligonucleotides and their respective targets is dependent upon the conditions under which that binding occurs. It is well known that binding, i.e. hybridization, between nucleic acid strands depends on factors besides the degree of mismatch between two sequences. Such factors include the GC content of the region, temperature, ionic strength, the presence of formamide and the types of counter ions present. The effect that these conditions have upon binding is known to one skilled in the art.

Furthermore, conditions are frequently determined by the circumstances of use. For example, when used in vivo, no formamide will be present and the ionic strength, types of counter ions, and temperature correspond to physiological conditions. Moreover, if selective detection in vitro of a specific target is desired stringent hybridization conditions are utilized to detect stable binding to only that target. If less selective detection is desired, e.g. to detect targets which are structurally related but not identical to a known target, non-stringent hybridization conditions can be employed. Binding conditions can therefore be manipulated in vitro to optimize the utility of the present oligonucleotides. A thorough treatment of the qualitative and quantitative considerations involved in establishing binding conditions permitting the skilled artisan to design oligonucleotides for use under the desired conditions is provided by Beltz et al., 1983, *Methods Enzymol.* 100:266–285 and by Sambrook et al. (1989, *Molecular Cloning: A Laboratory Manual,* Vols. 1–3, Cold Spring Harbor Press, NY).

As used herein "binding" or "stable binding" means that a sufficient amount of the oligonucleotide is bound or hybridized to its target to permit detection of that binding. Binding can be detected by either physical or functional properties of the target:stem-loop oligonucleotide complex.

Binding between a target and an oligonucleotide can be detected by any procedure known to one skilled in the art, including both functional or physical binding assays. Binding can be detected functionally by determining whether binding has an observable effect upon a biosynthetic process such as DNA replication, RNA transcription, protein translation and the like.

Physical methods of detecting the binding of complementary strands of DNA or RNA are well known in the art, and include such methods as DNase I or chemical footprinting, gel shift and affinity cleavage assays and light absorption detection procedures. For example, a method which is widely used, because it is so simple and reliable, involves observing a change in light absorption of a solution containing an oligonucleotide and a target nucleic acid at 220 to 300 nm as the temperature is slowly increased. If the oligonucleotide has bound to its target, there is a sudden increase in absorption at a characteristic temperature as the oligonucleotide and target dissociate or melt.

The binding between an oligonucleotide and its target nucleic acid is frequently characterized by the temperature at which 50% of the oligonucleotide is melted from its target. This temperature is the melting temperature ($T_m$). A higher $T_m$ means a stronger or more stable complex relative to a complex with a lower $T_m$. The stability of a duplex increases with increasing G:C content since G:C base pairs have three hydrogen bonds whereas A:T base pairs have two. The stem-loop oligonucleotides of the present invention bind to target with as many as two additional hydrogen bonds per base triad than a duplex nucleic acid containing only base pairs. Hence more stability is achieved since two binding domains are available for bonding to a single target nucleic acid, i.e. the P domain and the AP domain. Therefore, the triplex formed by a stem-loop oligonucleotide bound to its target nucleic acid melts at a higher $T_m$ than the duplex formed by a linear oligonucleotide and a target.

Figure 2A:
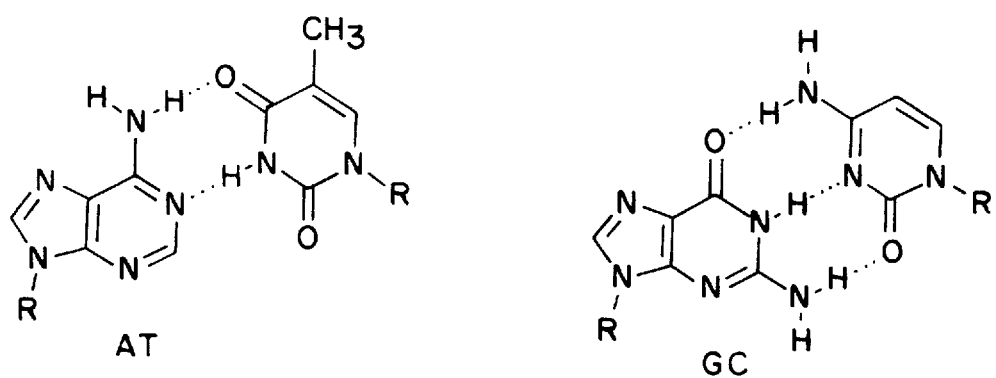
FIG. 2A depicts the bonding patterns of Watson-Crick (anti-parallel domain) AT and GC base pairs.
Figure 2B:
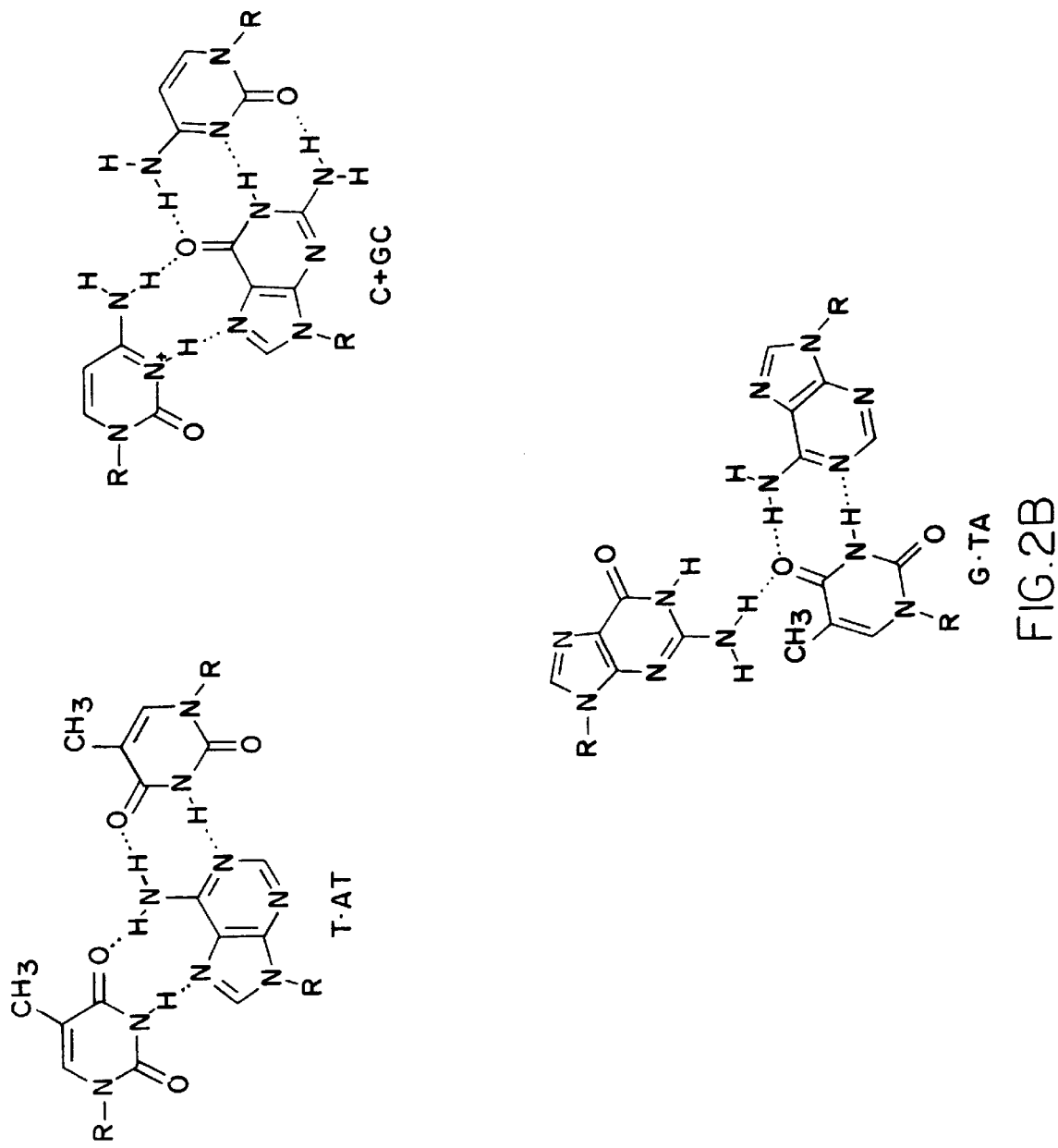
FIG. 2B depicts T-AT, C+GC and G-TA base triads that can form between P, target and AP nucleotides.

Stem-loop oligonucleotides bind to a nucleic acid target through hydrogen bonds formed between the nucleotides of the binding domains and the target. The AP domain can bind by forming Watson-Crick hydrogen bonds (e.g., FIG. 2a). The P domain can bind to the target nucleotides by forming non-Watson-Crick hydrogen bonds (e.g., FIG. 2b). When two nucleotides from different strands of DNA or RNA hydrogen bond by the base pairing rules defined herein, a base pair or duplex is formed. When a nucleotides from the P and AP domains both bind to the same target nucleotide, a base triad is formed.

Parallel domain base pairing with a complementary target strand of nucleic acid is thermodynamically less favorable than Watson-Crick base pairing; however, when both parallel and antiparallel pairing modes are present in a single molecule, highly stable complexes can form. Thus, two opposing domains of a stem-loop oligomer form a complex with a central target, giving a triplex structure, or a triple helical complex, bounded by the two ends of the loop. For example, this arrangement can allow formation of up to four hydrogen bonds when two thymines bind to a target adenine and up to five hydrogen bonds when two cytosines bind to a target guanine.

Furthermore, because of the binding characteristics of the P and AP domains, the present stem-loop oligonucleotides have a higher stability and selectivity for a particular target than do corresponding linear oligonucleotides. First, stem-loop oligonucleotides of this invention bind twice to the same central target strand. Hence two domains are involved in selecting a target. Second, protonation of cytosine in a C+G-C triad is favored only when this triad forms and the additional proton gives the triad a positive charge. This positive charge can lessen the negative charge repulsions arising from the juxtapositioning of three phosphodiester backbones.

Protonation of C+G-C triads occurs most readily at low pH and formation of C+G-C triads is favored over formation of many other triads at low pH. Therefore, P and AP domains which are cytosine-rich more stably bind a complementary guanine-rich target at low pH than cytosine-poor P and AP domains bind a guanine-poor target. The skilled artisan can take advantage of the effect of protonation upon C+G-C triad formation to design stem-loop oligonucleotides in accordance with the present invention whose selectivity for a target is enhanced if the pH of the hybridization reaction is known or can be adjusted. This is accomplished by selecting a guanine-rich target and constructing cytosine-rich P and AP binding domains if the hybridization pH is low, or by selecting a guanine-poor target and constructing cytosine-poor P and AP binding domains if the hybridization pH is high. For these purposes a low pH is about 5.0 to about 6.8, and preferably about 5.5, whereas a high pH is about 7.0 to about 9.0, and for use in vivo preferably about 7.4. As used herein, a cytosine-rich P or AP binding domain has about 2 to about 20 cytosines, and a guanine-rich target has about 2 to about 20 guanines. Conversely, a cytosine-poor P or AP binding domain has no more than one cytosine, while a guanine-poor target has no more than one guanine.

As described hereinabove, the stem-loop oligonucleotides of the present invention can be constructed to include more than one P or AP binding domain. Multiple pairs of binding domains permit binding of the oligonucleotide to more than one target. Alternatively, two or more pairs of binding domains can bind to the same target under different types of conditions.

For example, when binding to one target over another is desired the skilled artisan can make one set of P and AP domains cytosine-rich and another set cytosine-poor. Under such circumstances corresponding guanine-rich and guanine target sites are also selected for such multiple-binding domain oligonucleotides. The skilled artisan can then direct the stem-loop oligonucleotide to a particular target either by adjusting the pH or by taking advantage of natural variations in pH.

For example, two targets can be selected, a first target having many guanines and a second target with few guanines. A stem-loop oligonucleotide can be prepared to include a first pair of cytosine-rich AP and P binding domains complementary to the first target and a second pair of cytosine-poor AP and P binding domains complementary to the second target in accordance with the present invention. At low pH values, e.g. about pH 5.0 to 6.5, binding to the guanine-rich target is very highly favored whereas at high pH values, e.g. about pH 7.2 to 9.0, binding to the guanine-poor target is highly favored. Such oligonucleotides are therefore multifunctional, conformationally mobile ligands capable of controlled, selective binding to more than a single target site.

Moreover the selectivity of stem-loop oligonucleotides can be controlled by taking advantage of pH variations which occur naturally in vivo. For example, solid tumors can have a pH of 5.5 to 6.8 which is considerably lower than the average intracellular pH of 7.4 (Meyer et al., 1948, *Cancer Res.* 8:513).

Thus for the present invention, one of ordinary skill in the art can readily design a nucleotide sequence for the P and AP domains of the subject stem-loop oligonucleotides which exhibits sufficient complementarity to detectably bind to its target sequence.

Having designed the stem-loop oligonucleotide in accordance with the present invention as described hereinabove, the ordinarily skilled artisan can synthesize the oligonucleotides by methods known in the art. Preferably, the stem-loop oligonucleotides are made as linear oligonucleotides which naturally assume a stem-loop conformation under normal conditions, e.g. moderate pH and temperature conditions. As used herein a moderate pH is about 5.0 to about 8.5 and a moderate temperature is about 5° C. to about 42° C.

For most applications, the present stem-loop oligonucleotides are single-stranded DNA or RNA, with the bases guanine (G), adenine (A), thymine (T), cytosine (C) or uracil (U) in the nucleotides, or with any nucleotide analog that is capable of hydrogen bonding in a parallel or anti-parallel manner. Nucleotide analogs include pseudocytidine, isopseudocytidine, 3-aminophenyl-imidazole, 2'-O-methyladenonsine, 7-deazadenosine, 7-deazaguanosine, 4-acetylcytidine, 5-(carboxy-hydroxylmethyl)-uridine, 2'-O-methylcytidine, 5-carboxymethylaminomethyl-2-thioridine, 5-carboxymethylamino-methyluridine, dihydrouridine, 2'-O-methyluridine, 2'-O-methyl-pseudouridine, beta,D-galactosylqueosine, 2'-O-methylguanosine, inosine, N6-isopentenyladenosine, 1-methyladenosine, 1-methyl-pseudouridine, 1-methylguanosine, 1-methylinosine, 2,2-dimethylguanosine, 2-methyladenosine, 2-methylguanosine, 3-methylcytidine, 5-methylcytidine, 5-methyluridine, N6-methyl-adenosine, 7-methylguanosine, 5-methylamino-methyluridine, 5-methoxyaminomethyl-2-thiouridine, β-D-mannosylqueosine, 5-methoxycarbonylmethyluridine, 5-methoxyuridine, 2-methyl-thio-N6-isopentenyladenosine, N-(9-beta-D-ribofuranosyl- 2-methylthiopurine-6-yl)carbamoyl) threonine, N-(9-beta-D-ribofuranosylpurine-6-yl)-N-methylcarbamoyl)threonine. Either ribose or deoxyribose sugars can be used with these analogs. Nucleotide bases in an α-anomeric conformation can also be used in the stem-loop oligonucleotides of the present invention.

Preferred nucleotide analogs are unmodified G, A, T, C and U nucleotides; pyrimidine analogs with lower alkyl, lower alkoxy, lower alkylamine, phenyl or lower alkyl substituted phenyl groups in the 5 position of the base and purine analogs with similar groups in the 7 or 8 position of the base. Especially preferred nucleotide analogs are 5-methylcytosine, 5-methyluracil, diaminopurine, and nucleotides with a 2'-O-methylribose moiety in place of ribose or deoxyribose. As used herein lower alkyl, lower alkoxy and lower alkylamine contain from 1 to 6 carbon atoms and can be straight chain or branched. These groups include methyl, ethyl, propyl, isopropyl, butyl, isobutyl, tertiary butyl, amyl, hexyl, ethynyl, propynyl, butynyl, pentynyl, hexynyl, and the like. Preferred alkyl groups are methyl and propynyl.

The subject oligonucleotides can be made by any of a myriad of procedures known for making DNA or RNA oligonucleotides. For example, such procedures include chemical synthesis, enzymatic synthesis and recombinant synthesis.

Chemical synthesis of linear oligonucleotides is well-known in the art and can be achieved by solution or solid phase techniques. Moreover, linear oligonucleotides of defined sequence can be purchased commercially or can be made by any of several different synthetic procedures including the phosphoramidite, phosphite triester, H-phosphonate and phosphotriester methods, typically by automated synthesis methods. The synthesis method selected can depend on the length of the desired oligonucleotide and such choice is within the skill of the ordinary artisan. For example, the phosphoramidite and phosphite triester method produce oligonucleotides having 175 or more nucleotides while the H-phosphonate method works well for oligonucleotides of less than 100 nucleotides. If modified bases are incorporated into the oligonucleotide, and particularly if modified phosphodiester linkages are used, then the synthetic procedures are altered as needed according to known procedures. In this regard, Uhlmann et al. (1990, *Chemical Reviews* 90:543–584) provide references and outline procedures for making oligonucleotides with modified bases and modified phosphodiester linkages.

Enzymatic methods of DNA oligonucleotide synthesis frequently employ Klenow, T7, T4, Taq or *E. coli* DNA polymerases as described in Sambrook et al. Enzymatic methods of RNA oligonucleotide synthesis frequently employ SP6, T3 or T7 RNA polymerase as described in Sambrook et al. Reverse transcriptase can also be used to synthesize DNA from RNA (Sambrook et al.). Enzymatic synthesis of oligonucleotides requires a template nucleic acid which can either be synthesized chemically, or be obtained as mRNA, genomic DNA, cloned genomic DNA, cloned cDNA or other recombinant DNA. Some enzymatic methods of DNA oligonucleotide synthesis can require an additional primer oligonucleotide which can be synthesized chemically. Finally, linear oligonucleotides can be prepared by PCR techniques as described, for example, by Saiki et al., 1988, *Science* 239:487.

The present stem-loop oligonucleotides can be made recombinantly by placing a nucleic acid having a sequence which is complementary to the desired stem-loop oligonucleotide into an expression vector. Such an expression vector minimally encodes a segment which can effect expression of the stem-loop oligonucleotide when the segment is operably linked to the nucleic acid encoding the stem-loop oligonucleotide. However, such an expression vector can also encode additional elements such as origins of replication, selectable markers, transcription termination signals, centromeres, autonomous replication sequences.

As used herein, an expression vector can be a replicable or a non-replicable expression vector. A replicable expression vector can replicate either independently of host cell chromosomal DNA or by integration into host cell chromosomal DNA. Upon integration into host cell chromosomal DNA such an expression vector can lose some structural elements but retains the nucleic acid encoding the stem-loop oligonucleotide and a segment which can effect expression of the oligonucleotide. Therefore, the expression vectors of the present invention can be chromosomally integrating or chromosomally nonintegrating expression vectors.

Moreover, the present expression vectors can replicate in one host cell type, e.g., *Escherichia coli,* and undergo little or no replication in another host cell type, e.g., a mammalian or human cell type, so long as the expression vector permits expression of the present stem-loop oligonucleotides. Alternatively, the present expression vectors can replicate in more than one host cell type.

Expression vectors as described herein are DNA or RNA molecules engineered for controlled expression of a desired gene, i.e. a gene encoding the present stem-loop oligonucleotides. Such vectors also encode nucleic acid segments which are operably linked to nucleic acids encoding the stem-loop oligonucleotides. Operably linked in this context means that such segments can effect or cause expression of a stem-loop oligonucleotide of the present invention under at least one set of defined conditions. For example, the nucleic acid segments controlling expression of the present stem-loop oligonucleotides may be inducible, i.e. capable of effecting significant expression only when a specific inducer is present. Such an inducer can be a diffusible molecule, e.g. a sugar, phosphate, alcohol, metal ion, hormone and the like. However the inducer can also be a change in temperature or some other physical parameter.

Nucleic acid segments which can effect expression of the present oligonucleotides include promoters, enhancers, upstream control elements, transcription factor or repressor binding sites, termination signals and other elements which can control gene expression in the contemplated host cell. Preferably the vectors are plasmids, bacteriophages, cosmids or viruses.

Sambrook et al., 1989, Goeddel, 1990, Gene Expression Technology, *Methods in Enzymology,* Vol 185, Academic Press; Perbal, B. 1988, *A Practical Guide to Molecular Cloning,* John Wiley & Sons, Inc.; and Romanos et al. 1992, *Yeast* 8:423–488, provide detailed reviews of vectors into which a nucleic acid encoding the present stem-loop oligonucleotide can be inserted and expressed.

Expression vectors of the present invention function in prokaryotic, yeast or mammalian cells.

Prokaryotic expression vectors include bacterial and bacteriophage vectors that can transform such hosts as *E. coli, B. subtilis,* Streptomyces sps. and other microorganisms. Many of these vectors are based on pBR322 including pUC19 and pGEM-7Zf (commercially available from Promega, Madison, Wis.) and are well known in the art. Bacteriophage vectors that are used in the invention include lambda and M13.

Yeast vectors include the yeast $2\mu$ circle and derivatives thereof, yeast plasmids encoding yeast autonomous replication sequences, yeast minichromosomes, any yeast integrating vector and the like. A comprehensive listing of many types of yeast vectors is provided in Parent et al. (1985, *Yeast* 1:83–138).

Mammalian vectors can include SV40 based vectors, polyoma based vectors, adenovirus based vectors, retrovirus based vectors, Epstein-Barr virus based vectors, papovavirus based vectors, bovine papilloma virus (BPV) vectors, vaccinia virus vectors, baculovirus vectors and the like. Muzyczka (ed., 1992, *Curr. Top. Microbiol. Immunol.* 158:97–129) provides a comprehensive review of eukaryotic expression vectors.

Retroviral and adenoviral vectors are particularly preferred for delivery of the stem-loop oligonucleotides to a patient.

Elements or nucleic acid segments capable of effecting expression of a gene product include promoters, enhancer elements, upstream activating sequences, transcription termination signals and polyadenylation sites. All such promoter and transcriptional regulatory elements, singly or in combination, are contemplated for use in the present expression vectors. Moreover, genetically-engineered and mutated regulatory sequences are also contemplated herein.

Promoters are DNA sequence elements for controlling gene expression. In particular, promoters specify transcription initiation sites and can include a TATA box and upstream promoter elements.

Prokaryotic promoters that are contemplated by the present invention include, for example, the lac promoter, the trp promoter, the $P_L$ and $P_R$ promoters of lambda, the T7 polymerase promoter, the T3 polymerase promoter, the Sp6 polymerase promoter and the like.

Higher eukaryotic promoters which are useful in the present expression vectors include promoters of mammalian and viral origin. Viral promoters include promoters such as the baculovirus polyhedrin promoter, the vaccinia virus hemagglutinin (HA) promoter, SV40 early and late promoter, the herpes simplex thymidine kinase promoter, the Rous sarcoma virus LTR, the Moloney Leukemia Virus LTR, and the Murine Sarcoma Virus (MSV) LTR. Mammalian promoters include metallothionein, β-actin, γ-globin, β-globin, collagenase and heat shock protein (hsp) promoters. Such hsp promoters can be, for example, hsp70, hsp68, hsp72, hsp73 and similar promoters. Sambrook et al. (1989) and Goeddel (1990, Gene Expression Technology, *Methods in Enzymology,* Vol 185, Academic Press,) review higher eukaryote promoters.

Preferred promoters of the present invention include inducible promoters, i.e. promoters which direct transcription at an increased or decreased rate upon binding of a transcription factor. Transcription factors as used herein include any factor that can bind to a regulatory or control region of a promoter an thereby affect transcription. The synthesis or the promoter binding ability of a transcription factor within the host cell can be controlled by exposing the host to an inducer or removing an inducer from the host cell medium. Accordingly to regulate expression of an inducible promoter, an inducer is added or removed from the growth medium of the host cell. Such inducers can include sugars, phosphate, alcohol, metal ions, hormones, heat, cold and the like.

The expression vectors of the present invention can also encode selectable markers. Selectable markers are genetic functions that confer an identifiable trait upon a host cell so that cells transformed with a vector carrying the selectable marker can be distinguished from non-transformed cells. Inclusion of a selectable marker into a vector can also be used to ensure that genetic functions linked to the marker are retained in the host cell population. Such selectable markers can confer any easily identified dominant trait, e.g. drug resistance, the ability to synthesize or metabolize cellular nutrients and the like.

Accordingly, the present invention provides expression vectors for expressing the subject stem-loop oligonucleotides in a host cell. Such expression vectors can be placed in the host cell by known techniques. For example, prokaryotic, plant and mammalian host cells can be transformed with the present expression vectors by a variety of techniques including transfection, microinjection, infection and other transformation procedures. Transformation procedures include calcium-mediated, calcium phosphate-mediated, DEAE-dextran-mediated, polybrene-mediated transformation, protoplast or liposomal fusion, electroporation, microprojectile-mediated gene transfer and the like. Such procedures are provided in Izant et al. (1984, *Cell* 36:1007–1015); Klein et al. (1988, *Proc. Natl. Acad. Sci. USA* 85:4305); Sambrook et al., and the references cited therein. Thus, host cells comprising the expression vectors of the present invention are also provided herein.

Expression of the stem-loop oligonucleotides in vivo for use in vivo does not require purification. After chemical, enzymatic or recombinant synthesis, oligonucleotides may be purified by polyacrylamide gel electrophoresis, or by any of a number of chromatographic methods, including gel chromatography and high pressure liquid chromatography. To confirm a nucleotide sequence, oligonucleotides may be subjected to DNA sequencing by any of the known procedures, including Maxam and Gilbert sequencing, Sanger sequencing, capillary electrophoresis sequencing the wandering spot sequencing procedure or by using selective chemical degradation of oligonucleotides bound to Hybond paper. Sequences of short oligonucleotides can also be analyzed by plasma desorption mass spectroscopy or by fast atom bombardment (McNeal, et al., 1982, *J. Am. Chem. Soc.* 104:976; Viari, et al., 1987, *Biomed. Environ. Mass Spectrom.* 14:83; Grotjahn et al., 1982, *Nuc. Acid Res.* 10:4671). Sequencing methods are also available for RNA oligonucleotides.

As provided herein the stem of the present stem-loop oligonucleotides can be covalently cross-linked to effectively generate a covalently closed circle from the loop domain. In general such a cross-link can be an alkyl, a disulfide, an amine or a similar moiety which can be formed by known procedures. For example, an alkyl cross-link can be formed between the 7-nitrogen of one guanine residue and the 2-amine of another guanine using a bifunctional alkylating agent, e.g. a nitrogen mustard such as mechlorethamine (Calabresi et al., 1980, in Gilman et al. eds., *The Pharmacological Basis of Therapeutics,* MacMillan Publishing Co., Inc., pp.1256–1272). A disulfide cross-link can be formed by the method of Glick et al. (1992, *J. Am. Chem. Soc.* 114:5447–8). Therefore, formation of a stem-loop oligonucleotide with a covalently cross-linked stem is well within the ken of the skilled artisan.

The present invention also contemplates derivatization or chemical modification of the subject oligonucleotides with chemical groups to facilitate cellular uptake. For example, covalent linkage of one or more cholesterol moieties to an oligonucleotide can improve cellular uptake by 5- to 10-fold which in turn improves DNA binding by about 10-fold (Boutorin et al., 1989, FEBS Letters 254:129–132). In a preferred embodiment, a cholesterol moiety is linked to each end of the stem of the present stem-loop oligonucleotides.

Other ligands for cellular receptors may also have utility for improving cellular uptake, including, e.g. insulin, transferrin and others. Similarly, derivatization of oligonucleotides with poly-L-lysine can aid oligonucleotide uptake by cells (Schell, 1974, *Biochem. Biophys. Acta* 340:323, and Lemaitre et al., 1987, *Proc. Natl. Acad. Sci. USA* 84:648). Certain protein carriers can also facilitate cellular uptake of oligonucleotides, including, for example, serum albumin, nuclear proteins possessing signals for transport to the nucleus, and viral or bacterial proteins capable of cell membrane penetration. Therefore, protein carriers are useful when associated with or linked to the stem-loop oligonucleotides of this invention. Accordingly, the present invention contemplates derivatization of the subject stem-loop oligonucleotides with groups capable of facilitating cellular uptake, including hydrocarbons and non-polar groups, cholesterol, poly-L-lysine and proteins, as well as other aryl or steroid groups and polycations having analogous beneficial effects, such as phenyl or naphthyl groups, quinoline, anthracene or phenanthracene groups, fatty acids, fatty alcohols and sesquiterpenes, diterpenes and steroids.

Moreover, according to the present invention, the loop domains which do not encode a P or AP domain do not have to be composed of nucleotide bases. Non-nucleotide loop domains can make the present stem-loop oligonucleotides less expensive to produce. More significantly, stem-loop oligonucleotides with non-nucleotide loop domains are more resistant to nucleases and therefore have a longer biological half-life than linear oligonucleotides. Furthermore, non-nucleotide loop domains having no charge, or a positive charge, can be used to promote binding by eliminating negative charge repulsions between the loop and target. In addition, stem-loop oligonucleotides having uncharged or hydrophobic non-nucleotide loop domains can penetrate cellular membranes better than stem-loop oligonucleotides with nucleotide loops.

As contemplated herein, non-nucleotide loop domains can be composed of alkyl chains, polyethylene glycol or oligoethylene glycol chains or other chains providing the necessary steric or flexibility properties which are compatible with oligonucleotide synthesis.

The length of these chains is equivalent to about 2 to about 2000 nucleotides, with preferred lengths equivalent to about 3 to about 8 nucleotides. The most preferred length for these chains is equivalent to about 5 nucleotides.

Preferred chains for non-nucleotide loop domains are polyethylene glycol or oligoethylene glycol chains. In particular, oligoethylene glycol chains having a length similar to a 5 nucleotide chain, e.g. a pentaethylene glycol, a hexaethylene glycol or a heptaethylene glycol chain, are preferred.

Stem-loop oligonucleotides with non-nucleotide loop domains can be prepared by any known procedure.

For example, Durand et al. (1990, *Nucleic Acids Res.* 18:6353–6359) provides synthetic procedures for linking non-nucleotide chains to DNA. Such procedures can generally be adapted to permit an automated synthesis of a stem-loop oligonucleotide of the present invention.

In general, groups reactive with nucleotides in standard DNA synthesis, e.g. phosphoramidite, H-phosphonate, dimethoxytrityl, monomethoxytrityl and the like, can be placed at the ends of non-nucleotide chains and nucleotides corresponding to the ends of P and AP domains can be linked thereto.

The present invention further contemplates derivatization of the subject oligonucleotides with agents that can cleave or modify the target nucleic acid or other nucleic acid strands associated with or in the vicinity of the target. For example, viral DNA or RNA can be targeted for destruction without harming cellular nucleic acids by administering a stem-loop oligonucleotide complementary to the targeted nucleic acid which is linked to an agent that, upon binding, can cut or render the viral DNA or RNA inactive. Nucleic acid destroying agents that are contemplated by the present invention as having cleavage or modifying activities include, for example, RNA and DNA nucleases, ribozymes that can cleave RNA, azidoproflavine, acridine, EDTA/Fe, chloroethylamine, azidophenacyl, psoralen and phenanthroline/Cu. Uhlmann et al. (1990, *Chemical Reviews* 90:543–584) and Beaucage et al. (1993, *Tetrahedron* 49:1925–1963) provide further information on the use of such agents and methods of derivatizing oligonucleotides that can be adapted for use with the subject stem-loop oligonucleotides.

Therefore, derivatization of the subject stem-loop oligonucleotides with reporter molecules, nucleic acid destroying agents, drugs, groups that facilitate cellular uptake or groups that facilitate target binding can be done by any of the procedures known to one skilled in the art. Moreover, the desired groups can be added to nucleotides before or after synthesis of the oligonucleotide. For example, these groups can be linked to the 5-position of T or C and these modified T and C nucleotides can be used for synthesis of the present stem-loop oligonucleotides.

Derivatization of selected nucleotides permits incorporation of the group into selected domains of the stem-loop oligonucleotide. For example, in some instances it is preferable to incorporate certain groups into a portion of the loop where that group will not interfere with binding, or into an AP or P domain to facilitate cleavage or modification of the target nucleic acid.

The present invention further contemplates modification in the phosphodiester backbone of stem-loop oligonucleotides, e.g. as described in Dolnick (1991, *Cancer Invest.* 9:185–194). Such modifications can aid uptake of the oligonucleotide by cells or can extend the biological half-life of such nucleotides. For example, stem-loop oligonucleotides may penetrate the cell membrane more readily if the negative charge on the internucleotide phosphate is eliminated. This can be done by replacing the negatively charged phosphate oxygen with a methyl group, an amine or by changing the phosphodiester linkage into a phosphotriester linkage by addition of an alkyl group to the negatively charged phosphate oxygen. Alternatively, one or more of the phosphate atoms which is part of the normal phosphodiester linkage can be replaced. For example, NH—P, $CH_2$—P or S—P linkages can be formed. Accordingly, the present invention contemplates using methylphosphonates, phosphorothioates, phosphorodithioates, phosphotriesters and phosphorus-boron (Sood et al., 1990, *J. Am. Chem. Soc.* 112:9000) linkages. The phosphodiester group can be replaced with siloxane, carbonate, acetamidate or thioether groups.

These modifications can also increase the resistance of the subject oligonucleotides to nucleases. Methods for synthesis of oligonucleotides with modified phosphodiester linkages are reviewed by Uhlmann et al.

Additionally, different nucleotide sugars can be incorporated into the oligonucleotides of this invention. For example, RNA oligonucleotides can be used since RNA:DNA hybrids are more stable than DNA:DNA hybrids. A stem-loop oligonucleotide can comprise RNA in ony one domain, for example, the P domain. Additional binding stability can also be provided by using 2'-O-methyl ribose in the present stem-loop oligonucleotides. Phosphoramidite chemistry can be used to synthesize RNA oligonucleotides as described (Reese, C. B. In *Nucleic Acids & Molecular Biology;* Springer-Verlag: Berlin, 1989; Vol. 3, p. 164; and Rao et al., 1987, *Tetrahedron Lett.* 28:4897).

The synthesis of RNA 2'-O-methyloligoribonucleotides and DNA oligonucleotides differ only slightly. RNA 2'-O-methyloligonucleotides can be prepared with minor modifications of the amidite, H-phosphonate or phosphotriester methods (Shibahara et al., 1987, *Nucleic Acids Res.* 15:4403; Shibahara et al., 1989, *Nucleic Acids Res.* 17:239; Anoue et al., 1987, *Nucleic Acids Res.* 15:6131).

The present invention contemplates a variety of utilities for the subject stem-loop oligonucleotides which are made possible by their selective and stable binding properties with both single- and double-stranded targets. Some utilities include, but are not limited to: regulating biosynthesis of a DNA, RNA or protein encoded by providing a stem-loop oligonucleotide to a template for the DNA, the RNA or the protein; use of stem-loop oligonucleotides of defined sequence, bound to a solid support, for affinity isolation of complementary nucleic acids; use of the subject oligonucleotides to provide sequence specific stop signals during polymerase chain reaction (PCR); covalent attachment of a drug, drug analog or other therapeutic agent to stem-loop oligonucleotides to allow cell type specific drug delivery; and labeling stem-loop oligonucleotides with a detectable reporter molecule for localizing, quantitating or identifying complementary target nucleic One aspect of the present invention provides a method of regulating biosynthesis of a DNA, an RNA or a protein by expressing an RNA copy of at least one oligonucleotide of the present invention from an expression vector present in the mammalian cell. Such an RNA copy can bind to a target contained within a nucleic acid template for the DNA, the RNA or the protein and regulate biosynthesis of the DNA, the RNA or the protein.

Another aspect of the present invention provides a method of regulating biosynthesis of a DNA, an RNA or a protein by providing at least one oligonucleotide of the present invention with a nucleic acid template for the DNA, the RNA or the protein wherein the oligonucleotide can bind to a target sequence contained within the template under physiological conditions and regulate biosynthesis of the DNA, the RNA or the protein.

Moreover, the selectivity of stem-loop oligonucleotides can be controlled in vivo by taking advantage of natural pH variations between cancerous and non-cancerous tissues and by utilizing pairs of binding domains which bind to one target at low (tumor cell) pH and another target at higher (normal tissue) pH.

In particular, according to the present invention, the biosynthesis of a DNA, an RNA or a protein within a mammalian tumor cell can be selectively regulated, without substantially affecting such biosynthesis in non-tumor cells, e.g., a neighboring normal cell. This can be accomplished in accordance with the present invention by administering a stem-loop oligonucleotide having both a cytosine-rich pair of P and AP binding domains and a cytosine-poor pair of P and AP binding domains. The cytosine-rich binding domains bind to a target which is essential for cell function, and thereby regulate or inhibit that essential cell function. In contrast, the cytosine-poor P and AP domains bind to a target which is not essential for cell function and thereby have no significant impact upon cell function. Since the pH in such a solid tumor is lower than the pH of surrounding normal tissues, the stem-loop oligonucleotide preferentially binds to the guanine-rich target within the tumor. However, in normal tissues where the pH is higher, the stem-loop oligonucleotide has less preference for the guanine-rich target and binds to the guanine-poor target. Since the guanine-rich target is essential for cell growth or survival, and the guanine-poor target has a non-essential function, the growth of the tumor can thereby be regulated, e.g. inhibited or arrested.

The binding between the oligonucleotide and the target can, e.g. block access to the template or promote the degradation of the template, and thereby prevent proteins and nucleic acids involved in the biosynthetic process from binding to the template, from moving along the template, or from recognizing signals encoded within the template. For example, RNA templates bound by the subject stem-loop DNA oligonucleotides are susceptible to degradation by RNase H. Degradation of a selected RNA template thereby regulates use of the template in biosynthetic processes.

In accordance with the present invention, the stem-loop oligonucleotides can be DNA or RNA, and the nucleic acid targets can be DNA or RNA. In that DNA stem-loop oligonucleotides preferably bind DNA targets over RNA targets, the DNA oligonucleotides are useful in selecting DNA targets from a pool containing both DNA and RNA. RNA stem-loop oligonucleotides have a slight preference for RNA targets, and thus have similar utility in selecting RNA.

As provided by the present invention the nucleic acid templates can be RNA or DNA and can be single-stranded or double-stranded. For example, the P domain of the present stem-loop oligonucleotides can bind by non-Watson-Crick hydrogen bonding to one strand of a double-stranded target and promote displacement of the other strand by the AP domain.

As used herein, biosynthesis of a nucleic acid or a protein includes cellular and viral processes such as DNA replication, DNA reverse transcription, RNA transcription, RNA splicing, RNA polyadenylation, RNA translocation and protein translation, and of which can lead to production of DNA, RNA or protein, and involve a nucleic acid template at some stage of the biosynthetic process.

As used herein, regulating biosynthesis includes inhibiting, stopping, increasing, accelerating or delaying biosynthesis. Regulation may be direct or indirect. For example, biosynthesis of a DNA, RNA or protein may be regulated directly by binding a stem-loop oligonucleotide to the template for that DNA, RNA or protein. Alternatively, biosynthesis may be regulated indirectly by oligonucleotide binding to a second template encoding a protein that plays a role in regulating the biosynthesis of the first DNA, RNA or protein.

DNA replication from a DNA template is mediated by proteins which bind to an origin of replication, open the DNA and initiate DNA synthesis along the DNA template. To inhibit DNA replication in accordance with the present invention, stem-loop oligonucleotides are selected which bind to one or more targets in an origin of replication. Such binding blocks proteins involved in DNA replication from binding to the origin of replication. Therefore initiation or procession of DNA replication is inhibited. As an alternative method of inhibiting DNA replication, expression of the proteins which mediate DNA replication can be inhibited, for example, at the transcriptional or translational level. As one skilled in the art recognizes, DNA replication can also be increased, e.g. by inhibiting expression of a protein repressor of DNA replication.

DNA replication from an RNA template is mediated by the enzyme reverse transcriptase which binds to a replication start site in the template RNA also bound by a nucleic acid primer. To inhibit DNA replication from an RNA template, reverse transcriptase or primer binding can be blocked by binding a stem-loop oligonucleotide to the primer binding site, and thereby blocking access to that site. Moreover, inhibition of DNA replication can occur by binding a stem-loop oligonucleotide to a site residing in the RNA template since such binding can block access to that site and to downstream sites, i.e. sites on the 3' side of the target site.

To initiate RNA transcription, RNA polymerase recognizes and binds to specific start sequences, or promoters, on a DNA template. Binding of RNA polymerase opens the DNA template. There are also additional transcriptional regulatory elements that play a role in transcription and are located on the DNA template.

These transcriptional regulatory elements include enhancer sequences, upstream activating sequences, repressor binding sites and others. All such promoter and transcriptional regulatory elements, singly or in combination, are targets for the subject stem-loop oligonucleotides. Oligonucleotide binding to these sites can block RNA polymerase and transcription factors from gaining access to the template and thereby regulating, e.g., increasing or decreasing, the production of RNA, especially mRNA and tRNA. Additionally, the subject oligonucleotides can be targeted to the coding region or 3'-untranslated region of the DNA template to cause premature termination of transcription. One skilled in the art can readily design oligonucleotides for the above target sequences from the known sequence of these regulatory elements, from coding region sequences, and from consensus sequences.

RNA transcription can be increased by, for example, binding a stem-loop oligonucleotide to a negative transcriptional regulatory element or by inhibiting biosynthesis of a protein that can repress transcription. Negative transcriptional regulatory elements include repressor sites or operator sites, wherein a repressor protein binds and blocks transcription. Oligonucleotide binding to repressor or operator sites can block access of repressor proteins to their binding sites and thereby increase transcription.

The primary RNA transcript made in eukaryotic cells, or pre-mRNA, is subject to a number of maturation processes before being translocated into the cytoplasm for protein translation. In the nucleus, introns are removed from the pre-mRNA in splicing reactions. The 5' end of the mRNA is modified to form the 5' cap structure, thereby stabilizing the mRNA. Various bases can also be altered. The polyadenylation of the mRNA at the 3' end is thought to be linked with export from the nucleus. The subject stem-loop oligonucleotides can be used to block any of these processes.

A pre-mRNA template is spliced in the nucleus by ribonucleoproteins which bind to splice junctions and intron branch point sequences in the pre-mRNA. Consensus sequences for 5' and 3' splice junctions and for the intron branch point are known. For example, inhibition of ribonucleoprotein binding to the splice junctions or inhibition of covalent linkage of the 5' end of the intron to the intron branch point can block splicing. Maturation of a pre-mRNA template can, therefore, be blocked by preventing access to these sites, i.e. by binding stem-loop oligonucleotides of this invention to a 5' splice junction, an intron branch point or a 3' splice junction. Splicing of a specific pre-mRNA template can be inhibited by using stem-loop oligonucleotides with sequences that are complementary to the specific pre-mRNA splice junction(s) or intron branch point. In a further embodiment, a collection of related splicing of pre-mRNA templates can be inhibited by using a mixture of stem-loop oligonucleotides having a variety of sequences that, taken together, are complementary to the desired group of splice junction and intron branch point sequences.

Polyadenylation involves recognition and cleavage of a pre-mRNA by a specific RNA endonuclease at specific polyadenylation sites, followed by addition of a poly(A) tail onto the 3' end of the pre-mRNA. Hence, any of these steps can be inhibited by binding the subject oligonucleotides to the appropriate site.

RNA translocation from the nucleus to the cytoplasm of eukaryotic cells appears to require a poly(A) tail. Thus, a stem-loop oligonucleotide is designed in accordance with this invention to bind to the poly(A) tail and thereby block access to the poly (A) tail and inhibit RNA translocation. For such an oligonucleotide, both the P and AP domains can consist of about 6 to about 50 thymine residues. Preferred P and AP domain lengths for such an oligonucleotide are about 10 to about 20 thymine residues.

Protein biosynthesis begins with the binding of ribosomes to an mRNA template, followed by initiation and elongation of the amino acid chain via translational "reading" of the mRNA. Protein biosynthesis, or translation, can thus be blocked or inhibited using the subject stem-loop oligonucleotides to bind and block access to targets in the template mRNA. Such targets contemplated by this invention include the ribosome binding site (e.g. the Shine-Delgarno sequence), the 5' mRNA cap site, the initiation codon, and sites in the protein coding sequence. There are also classes of proteins which share domains of nucleotide sequence homology. Thus, inhibition of protein biosynthesis for such a class can be accomplished by targeting the homologous nucleotide and protein domains (via the coding sequence) with the subject stem-loop oligonucleotides.

Regulation of biosynthesis by any of the aforementioned procedures has utility for many applications. For example, genetic disorders can be corrected by inhibiting the production of mutant or over-produced proteins, or by increasing production of under-expressed proteins; the expression of genes encoding factors that regulate cell proliferation can be inhibited to control the spread of cancer; and virally encoded functions can be inhibited to combat viral infection.

In accordance with the present invention, it has been determined that in some instances the biosynthesis of a DNA, RNA or protein can more effectively be regulated by binding the template at more than one target site. The present stem-loop oligonucleotides which are prepared to bind to multiple target sites, e.g. by having more than one P or AP domain, are also effective in regulating the biosynthesis of a DNA, RNA or protein. For example, the binding of two sites within a gene can provide greater inhibition than achieved with single-site binding (Maher et al., 1987, *J. Arch. Biochem. Biophys.* 253:214–220; Tannock, I. F. in "The Basic Science of Oncology" 2nd ed.; Tannock, I. F. and Hill, R. P., eds. McGraw-Hill, New York, 348–349). In targeting viral sequences, the binding of two genes in a virus can inhibit viral replication more effectively than binding a single target. It has been shown, for example, that the use of multiple probes against a virus reduces the ability of the virus to escape inhibition by mutation (Kern et al., 1991, *Science* 252:1708–1711). A broader spectrum of inhibition by targeting two mutants of one virus or two viruses which are commonly found together, such as HIV-1 and cytomegalovirus (CMV) can also be achieved in accordance with the present invention.

Therefore, the present methods of regulating the biosynthesis of a DNA, RNA or protein can also include use of two or more stem-loop oligonucleotides or a stem-loop oligonucleotide with more than one pair of P and AP binding domains.

Some types of genetic disorders that can be treated by the stem-loop oligonucleotides of the present invention include Alzheimer's disease, some types of arthritis, sickle cell anemia and others. Many types of viral infections can be treated by utilizing the stem-loop oligonucleotides of the present invention, including infections caused by influenza, rhinovirus, human immunodeficiency virus (HIV), herpes simplex, papilloma virus, cytomegalovirus, Epstein-Barr virus, adenovirus, vesticular stomatitus virus, rotavirus, hepatitis A, B, C and D viruses and respiratory syncytial virus among others. According to the present invention, animal and plant viral infections may also be treated by administering the subject oligonucleotides.

Moreover, the present methods of regulating the biosynthesis of a DNA, RNA or protein can also be used to inhibit cellular oncogenes. Cellular protooncogenes are thought to have a normal role in cellular replication which is improperly executed when the protooncogene becomes mutated. Rather than controlling cellular growth, mutated protooncogenes, or oncogenes, can contribute to uncontrolled cellular growth and thereby increase the likelihood of developing cancer. The present methods can inhibit the transcription and translation of oncogenes such as, for example, oncogenes like the c-abl, bcr-abl, bcl-2, c-cbl, c-dbl, c-erb, c-ets, c-fgf, c-fms, c-fos, c-has/bas, her-2 neu, c-int, c-jun, c-kit, c-mas, c-met, c-mos, c-myb, c-myc, N-myc, p53, ras, c-Ha-ras, c-rel, c-ret, c-ros, c-sec, c-sis, c-ski, c-snoA, c-snoN, c-spi, c-src, c-syn, c-trk, c-vav and c-yes.

In another embodiment, the present methods for regulating the biosynthesis of a DNA, RNA or protein can be used to inhibit methods for inhibiting cancerous cell growth by binding such oligonucleotides to chromosomal sites normally bound by proteins, e.g. the p53 protein, whose normal function is to suppress uncontrolled cell division. Normally the p53 protein appears to inhibit cell growth, however mutant p53 proteins can have an opposite effect upon cell growth, causing uncontrolled cell division and a variety of cancers, especially sarcomas, breast, brain, adrenal cortex, colon, lung and leukemic cancers (Finlay et al., 1989, *Cell* 57:1083–1093; Ben-David et al., 1991, *Cell* 66:831–834; and Haber et al., 1991, *Cell* 64:5–8). Moreover, the p53 protein binds to DNA sites in a sequence-specific manner (Kern et al., 1991a, *Science* 252:1708–1711; Kern et al., 1991b, *Oncogene* 6:131–136).

Therefore, according to the present invention, the present stem-loop oligonucleotides and methods can be used to inhibit DNA replication and cell growth by binding to chromosomal sites normally bound by the p53 protein. For example, the nucleotide sequence SEQ ID NO:21 contains such a chromosomal site for p53 protein (Kern et al. 1991a *Science* 252:1708–1711; and European patent application 518,650 by Vogelstein et al.). The sequence of SEQ ID NO:21, is depicted below:

| 5'-TAAGCTTGAT | ATTCTCCCCA | GATGTAGTGA | AAGCAGGTAG |
|---|---|---|---|
| 3'-ATTCGAACTA | TAAGAGGGGT | CTACATCACT | TTCGTCCATC |
| ATTGCCTTGC | CTGGACTTGC | CTGGCCTTGC | CTTTTCTTTC |
| TAACGGAACG | GACCTGAACG | GACCGGAACG | GAAAAGAAAG |
| TTTCTTTCTT | TCTTTATTAC | TTTCTCTTTT | TCTTCTTCTT |
| AAAGAAAGAA | AGAAATAATG | AAAGAGAAAA | AGAAGAAGAA |
| CTTCTTCTTC | TTCTTCTTCT | TCTTCTTCTT | CTTCTTCTTC |
| GAAGAAGAAG | AAGAAGAAGA | AGAAGAAGAA | GAAGAAGAAG |
| TTCTTCTTCT | TTTTTTTTG | AGACAGAG-3' | |
| AAGAAGAAGA | AAAAAAAAAC | TCTGTCTC-5'. | |

Portions of SEQ ID NO:21 which can be chromosomal binding sites for p53 protein include but are not limited to positions 46–78 and positions 40–85 of SEQ ID NO:21.

The present invention also contemplates using the subject stem-loop oligonucleotides for targeting drugs to specific cell types. Such targeting can allow selective destruction or growth of particular cell types, e.g. inhibition of tumor cell growth can be attained. To target a drug to a specific cell type the skilled artisan takes advantage of the fact that different cell types express different genes, so that the concentration of a particular mRNA can be greater in one cell type relative to another cell type. An mRNA which is present in higher concentrations in the cell to which the drug is to be delivered is a suitable target mRNA. Cells with high concentrations of target mRNA are targeted for drug delivery by administering to the cell a stem-loop oligonucleotide which is complementary to the target mRNA and which has a covalently linked drug.

In the foregoing methods of use of the present stem-loop oligonucleotides in which in vivo use in a mammalian subject is contemplated, the oligonucleotides can be delivered by methods known to one of ordinary skill in the art. For example, the stem-loop oligonucleotide can be administered topically or parenterally, and can be modified, or conjugated, as disclosed hereinabove, or encapsulated into liposomes, to improve cellular uptake. The stem-loop oligonucleotides can also be carried and expressed by engineered retroviruses, or delivered by transfection in vitro into a patient's cells which are then re-infused into a patient. Such methods are disclosed for example by Tidd (1990, *Anticancer Research* 10:1169–1182); Carter et al (1993, *Br. J. Cancer* 67:869–876); and Gutierrez et al. (1992, *Lancet* 339:715–721).

In another aspect of the present invention, stem-loop oligonucleotides of defined sequence, bound to a solid support, can be used for affinity isolation of complementary nucleic acids. The subject stem-loop oligonucleotides can be attached to a solid support such as silica, cellulose, nylon, and other natural or synthetic materials that are used to make beads, filters, and column chromatography resins. Attachment procedures for nucleic acids to solid supports of these types are well known; any known attachment procedure is contemplated by the present invention. A stem-loop oligonucleotide attached to a solid support can then be used to isolate a complementary nucleic acid. Isolation of the complementary nucleic acid can be done by incorporating the oligonucleotide:solid support into a column for chromatographic procedures. Alternatively the oligonucleotide:solid support can be used for target nucleic acid isolation by filtration, sedimentation or centrifugation procedures.

Stem-loop oligonucleotide:solid supports can be used, for example, to isolate poly(A)$^+$ mRNA from total cellular or viral RNA when the stem-loop oligonucleotide has P and AP domain poly(dT) or poly(U) sequences. Stem-loop oligonucleotides are ideally suited to applications of this type because they are nuclease resistant and bind target nucleic acids so strongly.

Further utilities are available for the subject oligonucleotides in the field of polymerase chain reaction (PCR) technology. PCR technology provides methods of synthesizing a double-standard DNA fragment encoded in a nucleic acid template between two known nucleic acid sequences which are employed as primer binding sites. In some instances it is desirable to produce a single-stranded DNA fragment before or after having made some of the double stranded fragment. This can be done by, for example, binding a stem-loop oligonucleotide of the present invention to one of the primer binding sites or to a site lying between the primer binding sites.

The present invention also contemplates labeling the subject stem-loop oligonucleotides for use as probes to detect a target nucleic acid. Labeled stem-loop oligonucleotide probes have utility in diagnostic and analytical hybridization procedures for localizing, quantitating or detecting a target nucleic acid in tissues, chromosomes or in mixtures of nucleic acids.

Labeling of a stem-loop oligonucleotide can be accomplished by incorporating a "reporter molecule" into the subject stem-loop oligonucleotides by known procedures, e.g. as provided in Sambrook et al. or Beaucage et al. (1993, Tetrahedron 49:1925–1963). A "reporter molecule", as defined herein, is a molecule or atom which, by its chemical nature, provides an identifiable signal allowing detection of the stem-loop oligonucleotide. Detection can be either qualitative or quantitative.

The present invention contemplates using any commonly used reporter molecule including, for example, radionuclides, enzymes, fluorophores, biotins, digoxigenin, chemiluminescent molecules, bioluminescent molecules, avidin, streptavidin, psoralens, chelated heavy metals, and luciferin. The most commonly used reporter molecules are either enzymes, digoxigenin, radionuclides or fluorophores which can be linked to nucleotides in the stem-loop oligonucleotide either before or after oligonucleotide synthesis.

Commonly used enzymes include horseradish peroxidase, alkaline phosphatase, glucose oxidase and β-galactosidase, among others. Enzymes can be conjugated to avidin or streptavidin for use with a biotinylated probe. Similarly, nucleic acid probes can be conjugated to avidin or streptavidin for use with a biotinylated enzyme. The substrates to be used with the specific enzymes are generally chosen because a detectably colored product is formed by the enzyme acting upon the substrate. For example, p-nitrophenyl phosphate is suitable for use with alkaline phosphatase conjugates; for horseradish peroxidase, 1,2-phenylenediamine, 5-aminosalicyclic acid or toluidine are commonly used.

A digoxigenin reporter molecule can be detected by binding an anti-digoxigenin antibody which has conjugated thereto a second reporter molecule, e.g. an enzyme. The antibody-conjugated enzyme is then detected by application of a substrate for the enzyme.

Radionuclides are commonly used reporter molecules to form nucleic acid or oligonucleotide probes. Radionuclides can be incorporated into the present stem-loop oligonucleotides either during oligonucleotide synthesis or by end-labeling after oligonucleotide synthesis as described in Sambrook et al. To incorporate radionuclides during oligonucleotide synthesis radioactively labeled nucleotides are used, e.g. nucleotides with an $\alpha$-$^{32}$PO$_3$ moiety. Radionuclides can be incorporated after oligonucleotide synthesis by end labeling either the 3' or 5' end of the present stem-loop oligonucleotides. Such end labeling can be done enzymatically, e.g. a 5'-phosphate can be enzymatically removed with alkaline phosphatase and then replaced with a radioactively labeled 5'-phosphate, e.g. the $\gamma$-$^{32}$PO$_3$ from adenosine 5'-[$\gamma$-$^{32}$P]triphosphate, using T4 polynucleotide kinase. Radioactively labeled nucleotide triphosphates are readily available commercially.

Fluorophores that are readily available and suitable for the methods of the present invention include fluorescein isothiocyanate (FITC), rhodamine red and the like. Such fluorophores can be covalently linked to the present oligonucleotides by readily available procedures, e.g. as provided in Beaucage et al. (1993 Tetrahedron 49:1925–1963).

In one embodiment the present invention provides a stem-loop oligonucleotide probe which includes a donor fluorophore and an acceptor fluorophore, each fluorophore attached so that when the oligonucleotide probe is hybridized to a nucleic acid target the donor and acceptor fluorophores can undergo fluorescence resonance transfer.

The term fluorescent resonance energy transfer is an art-recognized term meaning that one fluorophore (the acceptor) can be promoted to an excited electronic state through quantum mechanical coupling with and receipt of energy from an electronically excited second fluorophore (the donor). This transfer of energy results in a decrease in visible fluorescence emission by the donor and an increase in fluorescent energy emission by the acceptor. However, significant energy transfer can only occur when the donor and acceptor are sufficiently closely positioned since the efficiency of energy transfer is highly dependent upon the distance between donor and acceptor fluorophores.

As used herein the donor and acceptor fluorophores are sufficiently closely positioned upon target hybridization by attaching the fluorophores to P and AP nucleotides which bind to the same target nucleotide or to neighboring target nucleotides. Donor and acceptor fluorophores can also be positioned on each end (i.e., 5' and 3') of stem-loop oligonucleotides having short stems, since such stem-loop oligonucleotides are linear in solution, but form stems when bound to a target.

Current hybridization techniques typically require that the hybridized probe be separated from unhybridized probe. Such a separation is generally accomplished by immobilizing a target nucleic acid sample onto a solid support, e.g. a filter or membrane, then performing the hybridization and finally washing off any unhybridized probe. However, such additional steps can be eliminated if the probe produces an identifiable change in signal upon hybridization. Therefore, the present stem-loop oligonucleotide probes which have donor and acceptor fluorophores positioned so that the fluorescence changes upon hybridization, can be used for detecting and quantitating a target nucleic acid in solution without separation of hybridized and unhybridized probes.

Therefore, stem-loop oligonucleotide probes linked to reporter molecules have utility in the detection of a specific DNA or RNA target by solution hybridization, as well as for example, Southern analysis, Northern analysis, in situ hybridization to tissue sections or chromosomal squashes and other analytical and diagnostic procedures. The methods of using such hybridization probes are well known and some examples of such methodology are provided by Sambrook et al.

The present stem-loop oligonucleotides can be used in conjunction with any known detection or diagnostic procedure which is based upon hybridization of a probe to a target nucleic acid. Moreover, the present stem-loop oligonucleotides can be used in any hybridization procedure which quantitates a target nucleic acid, e.g., by competitive hybridization between a target nucleic acid present in a sample and a labeled tracer target.

In another embodiment of the present invention, stem-loop oligonucleotides can accelerate the dissociation of a double-stranded nucleic acid target. Therefore the double-stranded nucleic acid target does not have to be subjected to denaturing conditions before binding of the present stem-loop oligonucleotides. Thus, the stem-loop oligonucleotides can bind to both single- and double-stranded nucleic acid targets under a wider variety of conditions, and particularly under physiological conditions. The present stem-loop oligonucleotides are several orders of magnitude faster at accelerating duplex nucleic acid strand displacement than are the corresponding linear oligonucleotides.

The present invention therefore provides method of strand displacement in a double-stranded nucleic acid target by providing the target with one of the subject stem-loop oligonucleotides for a time and under conditions effective to denature the target and permit the stem-loop oligonucleotide to bind to the target. The target for the present stem-loop oligonucleotides can be a double-stranded nucleic acid, either RNA or DNA, which has not undergone denaturation by, for example, heating or exposure to alkaline pH.

As used herein, the nucleic acids for strand displacement can be present in an organism or present in a sample which includes an impure or pure nucleic acid preparation, a tissue section, a prokaryotic or eukaryotic cell smear, a chromosomal squash and the like. Moreover, the nucleic acid targets for strand displacement by the present stem-loop oligonucleotides include viral, bacterial, fungal or mammalian nucleic acids.

According to the present invention, conditions effective for detectable denaturation of the target by strand displacement, thereby permitting a binding, can include having a suitable stem-loop oligonucleotide to target nucleic acid ratio. Moreover, as used herein a suitable ratio of stem-loop oligonucleotide to target is no less than 1.0. However, a slight excess is preferred, e.g. about 10 to about 10,000, or more preferably about 10 to about 100.

Moreover, as used herein a time effective to denature a double-stranded nucleic acid by strand-displacement with an oligonucleotide of the present invention is about 1 minute to about 16 hours.

A stem-loop oligonucleotide can associate with a duplex target by first binding in the P domain. Such P domain binding juxtaposes the AP domain nucleotides to compete for Watson-Crick binding to target nucleotide. This P domain pre-association followed by AP domain nucleotide competition for Watson-Crick binding may form the basis for the observed acceleration in strand displacement by stem-loop oligonucleotides.

The subject stem-loop oligonucleotides have three important features which enable duplex strand displacement. First, the stem-loop oligonucleotide has the ability to preassociate, e.g. by binding of a P domain to the target, which results in a high local concentration of P, AP and target. Second, the stem-loop oligonucleotide contains a second (i.e., AP), binding domain, which competes for binding to a complementary strand of the duplex. Finally, the stem-loop oligonucleotide binds with higher affinity than the displaced strand of the duplex, thereby driving the reaction to completion.

Furthermore, the reagents needed for making a stem-loop oligonucleotide probe and for utilizing such a probe in a hybridization procedure are provided in a kit.

The kit can be compartmentalized for ease of utility and can contain at least one stem-loop oligonucleotide. Additional containers providing reagents for labeling the stem-loop oligonucleotide with a reporter molecule or reagents for isolating the labeled stem-loop oligonucleotide can also be provided.

Moreover the present invention provides a kit for isolation of a template nucleic acid. Such a kit has at least one first container providing a stem-loop oligonucleotide which is complementary to a target contained within the template. For example, the template nucleic acid can be cellular and/or viral poly(A)$^+$ mRNA and the target can be the poly(A)$^+$ tail. Hence stem-loop oligonucleotides of the present invention which have utility for isolation of poly(A)$^+$ mRNA include P and AP domain sequences of poly(dT) or poly(U).

The kits can be compartmentalized to contain at least one first container providing a stem-loop oligonucleotide which can be linked to a reporter molecule. An additional container providing reagents for covalent linkage or detection of the reporter molecule can also be included in the kit.

Furthermore, the present invention provides kits useful for diagnosis which depends upon detection of a specific, known target nucleic acid. Such nucleic acid targets can be, for example, a viral nucleic acid, an extra or missing chromosome or gene, a mutant cellular gene or chromosome, an aberrantly expressed RNA and others. The stem-loop oligonucleotide(s) provided in these kits can bind to such targets and can have an attached reporter molecule.

Moreover, as contemplated by the present invention, the kits disclosed herein can include any elements recognized or conventionally used by the skilled artisan for constructing, purifying and using oligonucleotides.

A further aspect of this invention provides pharmaceutical compositions containing the subject stem-loop oligonucleotides with a pharmaceutically acceptable carrier. In particular, the subject oligonucleotides are provided in a therapeutically effective amount of about 0.1 µg to about 100 mg per kg of body weight per day, and preferably of about 0.1 µg to about 10 mg per kg of body weight per day, to bind to a nucleic acid in accordance with the methods of this invention. Dosages can be readily determined by one of ordinary skill in the art and formulated into the subject pharmaceutical compositions.

As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The subject oligonucleotides may be administered topically or parenterally by, for example, by osmotic pump, intraveneous, intramuscular, intraperitoneal subcutaneous or intradermal route, or when suitably protected, the subject oligonucleotides may be orally administered. The subject oligonucleotides may be incorporated into a cream, solution or suspension for topical administration. For oral administration, oligonucleotides may be protected by enclosure in a gelatin capsule. Oligonucleotides may be incorporated into liposomes or lipsomes modified with polyethylene glycol for parenteral administration. Incorporation of additional substances into the liposome, for example, antibodies reactive against membrane proteins found on specific target cells, can help target the oligonucleotides to specific cell types.

Moreover, the present invention contemplates administering the subject stem-loop oligonucleotides with an osmotic pump providing continuous infusion of such oligonucleotides, for example, as described in Ratajczak et al. (1992, *Proc. Natl. Acad. Sci. USA* 89:11823–11827). Such osmotic pumps are commercially available, e.g., from Alzet Inc (Palo Alto, Calif.).

Topical administration and parenteral administration in a liposomal carrier is preferred.

The following examples further illustrate the invention.

EXAMPLE 1

Strong Target Binding by Stem-Loop Oligonucleotides

Stem-loop oligonucleotides of the present invention bind target with greater stability than linear oligonucleotides which do not have a stem structure.

Materials and Methods

Oligonucleotide Synthesis and Purification

Oligonucleotides with SEQ ID NO:1–7 (see Table 1 for a partial listing) were synthesized on a Pharmacia LKB Gene Assembler Plus instrument using standard phosphoramidite chemistry (Beaucage et al., 1981 *Tetrahedron Lett.* 22:1859). β-Cyanoethyl phosphoramidite monomers were obtained commercially (Cruachem). Oligonucleotides were deprotected with 30% ammonia at 55° C. for 10 hr. and were purified by electrophoresis on 20% acrylamide gels with 7M urea and Tris●borate●EDTA buffer (Sambrook et al., 1989, *Molecular Cloning*, 2nd ed., Cold Spring Harbor Press). The oligonucleotide DNA was visualized by UV shadowing and excised from gels as a gel slice. Gel slices were crushed and oligonucleotide DNA was eluted at room temperature into 0.2N NaCl; this was followed by filtration and dialysis. Oligonucleotides were quantitated by absorbance at 260 nm using extinction coefficients which were calculated by the nearest neighbor method (Borer, P. N., 1975 in G. D. Fasman ed. *Handbook of Biochemistry and Molecular Biology* CRC Press, Cleveland, p. 589).

TABLE 1

Stem-Loop Oligonucleotides with SEQ ID NO:1–5

```
        TTTTTTTT                        SEQ ID NO:1
       C        C
  5'-C            T
                   C
  3'-C            T
       C        C
        TTTTTTTT

CTTTTTTT                        SEQ ID NO:2
       C        C
  5'-TCG          T
  3'-AGC          C
       C        T
       C        C
        TTTTTTTT

CTTTTTTT                        SEQ ID NO:3
       C        C
  5'-GCATCG       T
  3'-CGTAGC       C
       C        T
       C        C
        TTTTTTTT

CTTTTTTT                        SEQ ID NO:4
       C        C
  5'-GCAGCATCG    T
  3'-CGTCGTAGC    C
       C        T
       C        C
        TTTTTTTT

CTTTTTTT                        SEQ ID NO:5
       C        C
  5'-GCAGCAGCATCG T
  3'-CGTCGTCGTAGC C
       C        T
       C        C
        TTTTTTTT
```

Thermal Denaturation Methods

Melting studies were carried out using a Gilford 250 UV-vis spectrophotometer equipped with a Gilford 2527 thermocontroller, as described previously (Prakash et al., 1991, *J. Chem. Soc. Chem. Commun.*:1161). Melting study solutions contained 3 μM of each oligonucleotide, unless specified otherwise, in a buffer of 10 mM $MgCl_2$, 100 mM NaCl, and 10 mM $KHOP_4$ (pH 7.0) (Turner et al., 1988, *Ann. Rev. Biophys. Chem.* 17:167–192). Absorbances were measured in stoppered 0.1 cm-pathlength cells under nitrogen atmosphere. Temperature was increased from 0° to 90° C. at a rate of 1 degree per minute. Melting temperatures ($T_m$) were taken to be the temperature of half-dissociation and were obtained from a plot of the derivative of 1/T vs. absorbance at 260 nm. Precision in $T_m$ values, estimated from variance in multiple experiments, is ±0.50° C.

Results

Thermal denaturation studies at pH 7.0 confirm that the four oligonucleotides with potential stem structures form stem-loop hairpins.

FIG. 3 depicts the melting temperatures ($T_m$) of oligonucleotides having varying stem lengths. The observed $T_m$'s rise with increasing stem length from 15° C. for the 3-base stem to 75° C. for the twelve-base stem. The data indicate no stem-loop intermolecular complexes formed. In particular, $T_m$'s measured over at least three different concentrations in the range 3–20 μM for each oligonucleotide did not change significantly, indicating that intramolecular rather than intermolecular hybridization is dominant.

Triple Helical Complexes

Hybridization studies of stem-loop oligonucleotides with the complementary $dA_8$ target (i.e. SEQ ID NO:6) confirm that bimolecular complexes are formed when a complementary target is present. These hybridization experiments further indicate that the complexes formed between stem-loop oligonucleotides and target are considerably stronger than the comparable Watson-Crick duplex, e.g. $dA_8 \bullet dT_8$, under the same conditions.

FIG. 4 compares the melting curves for the SEQ ID NO:5 oligonucleotide with and without the SEQ ID NO:6 ($dA_8$) target. Without the $dA_8$ target, the SEQ ID NO:5 oligonucleotide had a single melting transition at 75° C. Consistent with the data provided in FIG. 3, this 75° C. $T_m$ was due to the dissociation of the intramolecular stem hydrogen bonds. When the target was present, two melting transitions were observed, one at 75° C., and one at a lower temperature of 42° C. The lower transition thus corresponds to the dissociation of the complementary $dA_8$ target, and the higher transition corresponds to the melting of the stem.

The observation of a melting transition below 75° C. indicates that the P and AP domains of the SEQ ID NO:5 stem-loop oligonucleotide simultaneously melt from target.

In comparing the hyperchromicities upon melting, the stem duplex dissociation had an approximate change in hyperchromicity of 9%, while the triplex dissociation had a change of about ~20%. The higher change in hyperchromicity upon triplex dissociation may be due to unstacking of a greater number of bases when the SEQ ID NO:5-triple helix melts than when the duplex stem melts.

The proportion of target present in a complex of SEQ ID NO:2 stem-loop and SEQ ID NO:6 target was varied in mixing experiments to determine what mole fraction of target was present at complete complexation with stem-loop oligonucleotide. The total DNA concentration was maintained at 4.5 μM while the proportion of target to stem-loop oligonucleotide was varied. Binding was detected by observing changes in absorbance at 260 nm.

Under conditions of constant DNA concentration, a change in the slope of observed absorbance vs target mole fraction indicates that no further binding to stem-loop oligonucleotide will occur as the proportion of target is increased. Therefore the inflection point in such a curve provides the mole fraction at which complete complexation has occurred. If the inflection point is approximately 0.5 then half of the oligonucleotide present in the hybridized complex is the stem-loop oligonucleotide and half is a target oligonucleotide. Accordingly a mole fraction of about 0.5 for complete complexation indicates the stoichiometry of target to stem-loop oligonucleotide is 1:1.

When the mole fraction for complete complexation is less than 0.5, less target than stem-loop oligonucleotide is present in the complex, e.g., a mole fraction of 0.33 means that one target oligonucleotide is bound per two stem-loop oligonucleotides. Under such circumstances the stoichiometry of target to stem-loop oligonucleotide in the complex will be less than 1:1. Similarly, when the mole fraction for complete complexation is greater than 0.5, more target than stem-loop oligonucleotide is present in the complex. For example, if separate target molecules are bound to the P and AP domains in a stem-loop oligonucleotide, the observed mole fraction at complete complexation will be greater than 0.5 and the stoichiometry of target to stem-loop is be greater than 1:1.

FIG. 5 shows a mixing curve of the $dA_8$ target with the SEQ ID NO:2 oligonucleotide. If P and AP binding domains of the stem-loop oligonucleotide bound separate targets, two equivalents of target will be present and the mole fraction will be greater than 0.5. Instead, FIG. 5 demonstrates that the mole fraction for complete complexation was about 0.5. Therefore the complex formed with a 1:1 stoichiometry. These data indicate that both the P and AP domains contributed to binding a single target. Accordingly the complex was triple helical.

The complex stability of two nearly identical stem-loop oligonucleotides further evidences a triple helical structure upon binding of target. In particular, the SEQ ID NO:8 oligonucleotide has a single mismatched base (a cytosine) in the P binding domain relative to the SEQ ID NO:2 oligonucleotide. A complex formed between the $dA_8$ target and the SEQ ID NO:2 oligonucleotide has a $T_m$ of 34.0° C., while the complex formed with the SEQ ID NO:8 oligonucleotide has a $T_m$ which is only 25.6° C. (see Table 2).

TABLE 2

Effect of Mismatch Upon Melting Temperature

```
              C T T T T T T T T C              SEQ ID NO:2
            C | | | | | | | | | T
    5'-T C G   A A A A A A A A
        A G C                                   C
            C | | | | | | | | | T
              C T T T T T T T T C

T_m = 34.0° C.

C T T T C T T T T C              SEQ ID NO:8
            C | | |   | | | | | T
    5'-T C G   A A A A A A A A
        A G C                                   C
            C | | | | | | | | | T
              C T T T T T T T T C

T_m = 25.6° C.
```

The presence of this one mismatch in the P binding domain therefore yielded a considerably weaker complex, i.e. a $T_m$ which is 8.4° C. lower than the fully complementary complex. The difference in observed $T_m$ values clearly indicates that both P and AP binding domains are involved in binding. If only the AP binding domains contributed to binding, no difference in $T_m$ values would be observed.

Moreover, the hyperchromicity associated with dissociation of the fully complementary complex was 20%, while the mismatched complex had a hyperchromicity of only 15%. The fully complementary complex also exhibited a clear melting transition at 284 nm, a wavelength at which triple helices composed entirely of T-A-T base triads display significant changes in absorbance, but at which A-T Watson-Crick duplexes do not (Riley et al., 1966 *J. Mol. Biol.* 20:359–389). These data therefore further evidence a larger number of hydrogen bonds in the fully complementary complex.

FIG. 6 depicts melting curves for complexes formed between the SEQ ID NO:1–5 stem-loop oligonucleotides and the SEQ ID NO:6 target. Table 3 summarizes the observed melting temperatures for these complexes, compared to the $dA_8 \bullet dT_8$ duplex. These data indicate that all $T_m$'s for stem-loop oligonucleotide: target complexes are considerably higher than for a corresponding the duplex.

In particular, the $dA_8 \bullet dT_8$ duplex melts at only ~11° C. In contrast, the SEQ ID NO:1 oligonucleotide which has no stem had a $T_m$ of 32.2° C., i.e., a $T_m$ increase of 21° C. over the duplex.

Closure of the loop by addition of Watson-Crick stems further increases the stability of target binding. In fact addition of even a three-base pair stem increased the binding stability with target. For example, $T_m$ values for complexes formed between target and stem-loop oligonucleotides having from 3 to 12 stem base pairs range from 34.0° C. to 40.4° C. (Table 3). Therefore, even a short three-base stem domain conferred an additional 1.8° C. of stability relative to a stemless loop. However, there is no additional advantage to a stem length greater than six base pairs (FIG. 7).

Accordingly, inclusion of P, AP and stem domains within an oligonucleotide provides an oligonucleotide with the necessary structural domains to achieve 23° to 29° C. greater stability than a corresponding Watson-Crick duplex.

TABLE 3

Melting Temperatures of SEQ ID NO:1–5 and 7 Oligonucleotides with the $dA_8$ Target

| SEQ ID NO:7 | AAAAAAAA<br>\|\|\|\|\|\|\|\|<br>TTTTTTTT | $T_m = 11°$ C. |
|---|---|---|
| SEQ ID NO:1 | TTTTTTTT<br>C\|\|\|\|\|\|\|\|C<br>5'-C         T<br>    AAAAAAAA   C<br>3'-C         T<br>C\|\|\|\|\|\|\|\|C<br>TTTTTTTT | $T_m = 32.2°$ C. |
| SEQ ID NO:2 | TTTTTTTT<br>C\|\|\|\|\|\|\|\|C<br>5'-TCG         T<br>3'-AGC AAAAAAAA   C<br>C\|\|\|\|\|\|\|\|T<br>C\|\|\|\|\|\|\|\|C<br>TTTTTTTT | $T_m = 34.0°$ C. |
| SEQ ID NO:3 | CTTTTTTTT<br>C\|\|\|\|\|\|\|\|C<br>5'-GCATCG       T<br>3'-CGTAGC AAAAAAAA   C<br>C\|\|\|\|\|\|\|\|T<br>C\|\|\|\|\|\|\|\|C<br>TTTTTTTT | $T_m = 40.4°$ C. |
| SEQ ID NO:4 | CTTTTTTTT<br>C\|\|\|\|\|\|\|\|C<br>5'-GCAGCATCG       T<br>3'-CGTCGTAGC AAAAAAAA   C<br>C\|\|\|\|\|\|\|\|T<br>C\|\|\|\|\|\|\|\|C<br>TTTTTTTT | $T_m = 39.6°$ C. |
| SEQ ID NO:5 | CTTTTTTTT<br>C\|\|\|\|\|\|\|\|C<br>5'-GCAGCAGCATCG     T<br>3'-CGTCGTCGTAGC AAAAAAAA   C<br>C\|\|\|\|\|\|\|\|T<br>C\|\|\|\|\|\|\|\|C<br>TTTTTTTT | $T_m = 38.7°$ C. |

Moreover, the target binding stability of a stem-loop oligonucleotide approached that of a covalently closed circular oligonucleotide. In particular a complex formed between the SEQ ID NO:6 target and a stem-loop oligonucleotide with a 6-base stem had a $T_m$ of 40.4° C. while a $T_m$ of 44.8° C. was measured for a complex of a structurally similar circle with the SEQ ID NO:6 target (Prakash et al., 1991 *J. Am. Chem. Soc.* 114:3523). Therefore, a stem-loop oligonucleotide can achieve a $T_m$ which is within about 4° C. of the $T_m$ observed for a circular oligonucleotide having the same P and AP binding domains.

Binding to Long Targets

When binding to complementary sites within longer targets, stem-loop oligonucleotides have non-binding domains which pass over the nucleic acids flanking the target site. To observe how such flanking nucleic acids effect the stability of a stem-loop oligonucleotide:target complex, a longer target was synthesized (SEQ ID NO:9). The melting temperatures of the SEQ ID NO:3 stem-loop oligonucleotides bound to the short target $dA_8$ (SEQ ID NO:6) and to this longer SEQ ID NO:9 target were then measured.

A complex formed between the longer target (SEQ ID NO:9) and the SEQ ID NO:3 stem-loop oligonucleotide had a melting temperature of 38.3° C., similar to the melting temperature of a complex between a short target (SEQ ID NO:6) and the same stem-loop oligonucleotide (40.4° C.). Therefore, the complex with the longer target had a $T_m$ which was only 1.8° C. lower than with the short target. However, the $T_m$ of the longer target was still 20° C. higher than the Watson-Crick duplex $dT_8 \bullet dA_8$. This result establishes that stable complex formation can occur between stem-loop oligonucleotides and longer targets which are likely to occur naturally.

EXAMPLE 2

Stem-Loop Oligonucleotides Bind Target More Selectively Than Linear Oligonucleotides In order to measure the sequence selectivity of stem-loop oligonucleotides, a set of target oligonucleotides with one variable base are constructed. Binding energies for a stem-loop oligonucleotide complexed with these targets are measured. The selectivity is defined by the free energy difference observed for a fully complementary target and a mismatched target. The selectivity obtained with the stem-loop structure is then directly compared to the selectivity of an analogous linear oligonucleotide.

Materials and Methods

DNA oligonucleotides are machine synthesized using the β-cyanoethyl phosphoramidite method as described in Example 1.

The sequence selectivity of a stem-loop oligonucleotide with SEQ ID NO:10 is measured by hybridization with targets which contained a single mismatched base. The strength ($\Delta G°_{37}$) of the resulting complexes is measured by thermal denaturation.

Eight targets are synthesized which are complementary to the SEQ ID NO:10 stem-loop oligonucleotide. However each target has a single centrally positioned variable base defined as N which could be any one of A, G, C or T. Four targets with a variable base N at position 5 could match two opposing T's in an equivalent position of the SEQ ID NO:10 stem-loop oligonucleotide, resulting in a T-N-T triad. The other four targets have a variable base N at position 8 which can match with two opposing C's in an equivalent position of the SEQ ID NO:10 stem-loop oligonucleotide, giving a C-N-C triad.

For comparison to the complex formed with the stem-loop oligonucleotide, a linear oligonucleotide (SEQ ID NO:11) is tested which has a sequence equivalent to the AP domain of SEQ ID NO:10. The linear SEQ ID NO:11 oligonucleotide can form a duplex with targets to form either a central T-N pair or a central C-N pair.

TABLE 4

Oligonucleotides for Binding Selectivity Tests

| complex (X, Y = A, T, G, C) | Stem-Loop or Linear Oligo SEQ ID NO: | Target SEQ ID NO: |
|---|---|---|
| 3'-TTCTTTTCTTTC<br>    \|\|\|\| \|\|\|\|\|\|\|\|<br>5'-AAGA<u>N</u>AAGAAAG | 11 | 12 |
|            CTTCTTTTCTTTCC<br>      A \|\|\|\| \|\|\|\|\|\|\|\| A<br>5'-GCATCG   AAGANAAGAAAG  C<br>3'-CGTAGC   \|\|\|\|T\|\|\|\|\|\|\|  A<br>      A \|\|\|\|\|\|\|\|\|\|\|\| C<br>           CTTCTTTTCTTTC | 10 | 12 |
| 3'-TTCTTTTCTTTC<br>   \|\|\|\|\|\|\|\| \|\|\|\|<br>5'-AAGAAAA<u>N</u>AAG | 11 | 13 |
|            CTTCTTTTCTTTCC<br>      A \|\|\|\|\|\|\|\| \|\|\|\| A<br>5'-GCATCG   AAGAAAANAAG  C<br>   CGTAGC   \|\|\|\|\|\|\|\|T\|\|\|  A<br>      A \|\|\|\|\|\|\|\|\|\|\|\| C<br>           CTTCTTTTCTTTC | 10 | 13 |

Thermal denaturations of the sixteen complexes are carried out in the presence of 10 mM MgCl₂, 100 mM NaCl, and 10 mM Tris●HCl (pH 7.0), with target and stem-loop or linear oligonucleotide concentrations at about 3 μM each. Experiments are carried out in duplicate and the results averaged. Oligonucleotide:target complex melting is monitored at 260 nm. The temperature vs. absorbance curves will have a single transition from bound to free oligonucleotide. Free energies of association are obtained by fitting the data with a two-state curve-fitting method. The results are verified by measuring association energies by the van't Hoff method. Selectivities are defined as the difference in free energies (ΔG) of complexation between matched and mismatched oliogmers.

Results

The correct match for the duplex (SEQ ID NO:11 and 12 or SEQ ID NO:11 and 13) yields the most favorable complex, whereas mismatches in the AT of duplex are expected to result in a loss of about 3.2–4.4 kcal/mol in binding energy, as illustrated by published mismatch studies. Mismatches in the GC of the duplex can result in a loss of about 5.2 to 5.8 kcal/mol of binding energy, as shown by published data.

The effects of a T-N-T mismatch on stem-loop oligonucleotide binding strength can be more dramatic. Once again, the true match (N=A) provides the most favorable three stranded complexes. However, target mismatches (N=G, T, C) result in a considerably larger loss of binding energy for a stem-loop oligonucleotide than for a linear oligonucleotide. The effect of a C-N-C mismatch in the three stranded complex similarly causes a larger loss in binding energy than a mismatch in a duplex.

Thus, the stem-loop ligand can have greater selectivity for its correctly matched sequence than does the standard linear oligomer. There are two factors which may explain this high selectivity. First, because two domains of the stem-loop oligonucleotide bind the central target strand, the stem-loop oligonucleotide, in effect, checks the sequence twice for correct matching. Secondly, protonation of cytosine within a C+G-C triad may also be a factor in increasing selectivity.

This protonation is likely to be favored only when there is base triad formation wherein guanine can share the positive charge; evidence suggests that the pKa of cytosine within a base triad is 2–3 units higher than that of free deoxycytosine. The addition of this positive charge may lessen the negative charge repulsions arising from the high density of phosphates in the complex and thereby increase binding stability.

Therefore, stem-loop oligonucleotides, as described herein, have both higher binding affinity and higher selectivity than can be achieved with Watson-Crick duplexes alone.

EXAMPLE 3

Factors Effecting Complex Formation

1) Solution effects. The effects of NaCl, $Mg^{2+}$, spermine, and pH on stem-loop:target complexes are examined. Stem-loop oligonucleotides with cytosines in the binding domains are sensitive to pH, and have greater stability at lower pH values. However, these and other stem-loop:target complexes are quite stable at the physiological pH of 7.0–7.4. The complexes have salt concentration sensitivity comparable to duplexes; however, small physiological amounts of $Mg^{2+}$ or spermine can increase the complex stability markedly. Therefore, stem-loop:target complexes are stable under physiological conditions.

2) Optimal number of nucleotides separating the P and AP domains. The optimum number of nucleotides separating P and AP domains is determined by observing the stability of complex formation between target and stem-loop oligonucleotides having different loop sizes but constant P and AP domain sizes. Stem-loop oligonucleotides with 2, 3, 4, 5, 6 and 10 bases separating the P and AP domains are tested. Each of the stem-loop oligonucleotides are designed to bind to the $dA_8$ target (i.e. SEQ ID NO: 6).

The $T_m$'s for stem-loop oligonucleotides with 4, 5, 6 and 10 bases separating the P and AP indicate that a separation of five nucleotides is optimal.

3) Binding Domain length. The melting temperatures of stem-loop oligonucleotides having different length binding domains are observed to ascertain optimal length, particularly with reference to the optimal size of a corresponding duplex. Therefore, stem-loop oligonucleotides with various size binding domains are made and complexed with single-stranded $dA_n$ targets, wherein n is 4, 8, 12 and 18 nucleotides.

Considerably higher $T_m$'s are observed for stem-loop:target complexes relative to Watson-Crick duplexes having the same length binding domains. For example, a stem-loop complex with 12-base binding domains can melt at about the same temperature as a 24-base duplex.

4) Methylation. It has been known for some time that methylation at the C-5 position of cytosine, forming the naturally-occurring base $m^5C$, raises the $T_m$ of duplex DNA in which it occurs, relative to unmethylated sequences (Zmudzka et al., 1969, Biochemistry 8:3049). In order to investigate whether addition of this methyl group would stabilize stem-loop:target complexes, the melting temperatures of methylated and unmethylated stem-loop oligonucleotides are compared. Use of the natural base $m^5C$ in place of C can increase stability substantially.

EXAMPLE 4

Replacement of Nucleotide Loop Domains with Non-Nucleotide Loop Domains

The domains separating P and AP binding domains of stem-loop oligonucleotides can be replaced with polyethylene or oligoethylene glycol chains.

Methods

Stem-loop oligonucleotides are synthesized with varying numbers of ethylene glycol repeats at precise positions. In each case the ethylene glycol chain is synthetically prepared for automated DNA synthetic procedures using the method of Durand et al. (1990, *Nucleic Acids Res.* 18:6353–6359). Briefly, a phosphoramidite is placed on a hydroxy group at one end of the ethylene glycol chain and a dimethoxytrityl (DMT) moiety is placed on the other terminal ethylene glycol hydroxy group. This derivatized ethylene glycol chain can then be added to the growing linear oligonucleotide at the appropriate step of automated DNA synthesis.

The melting temperatures (Tm) of stem-loop oligonucleotides with polyethylene loop domains are observed to determine an optimal polyethylene glycol chain length for separating the P and AP binding domains. Such measurements are obtained at pH 7.0 (10 mM Tris-HCl) in 10 mM $MgCl_2$ and 100 mM NaCl. For such experiments, each target and stem-loop oligonucleotide are present at a concentration of about 3 μM.

Stem-loop oligonucleotides with hexaethylene glycol loop domains separating the P and AP binding domains bind with greater stability than do stem-loop oligonucleotides with tetra- or penta-ethylene glycol loop domains.

Nuclease Resistance

The nuclease resistance of stem-loop and linear oligonucleotides are compared when these oligonucleotides are incubated in human plasma for varying time periods. Stem-loop and linear oligonucleotides having similar numbers of nucleotides are incubated at about a 50 μM concentration in plasma at 37° C. Aliquots are removed at various time points and cleavage products are separated by gel electrophoresis. Nuclease resistance is assessed by observing whether degradation products are evident on the gels.

When incubated in human plasma the half-life of linear oligonucleotide 2 is about 20 min. In contrast, a stem-loop oligonucleotide can undergo little or no nuclease degradation during this time period. Accordingly, the half-life of a stem-loop oligonucleotide can be much greater than a linear oligonucleotide containing the same number of nucleotides but having no stem structure (e.g., see Tang et al., 1993, *Nucleic Acids Res.* 21:2729–2735).

EXAMPLE 5

Strand Replacement By Stem-Loop Oligonucleotides

The stem-loop oligonucleotide with SEQ ID NO:3 binds to a $dA_8$ target with 29° C. greater stability than a corresponding linear $dT_8$ oligonucleotide (Example 1). Such an increase in stability demonstrates that a stem-loop oligonucleotide:target complex is thermodynamically favored over a linear oligonucleotide:target. In addition, a stem-loop oligonucleotide can accelerate (or catalyze) dissociation of duplex DNA target sequences to form a complex with one strand of the duplex.

To test whether a stem-loop oligonucleotide can readily dissociate duplex DNA and displace one strand of a duplex DNA target, the kinetics of strand displacement are observed for a duplex DNA target in the presence of a complementary linear or a complementary stem-loop oligonucleotide.

A DNA duplex target with a fluorescein group on one strand and a tetramethylrhodamine group on the other strand is prepared using published procedures (Cardullo et al., 1988, *Proc. Natl. Acad. Sci. USA* 85:8790; Cooper et al., 1990, *Biochemistry* 29:9261). The structure of the duplex target (SEQ ID NO:18) is depicted below:

The Tm of this labeled duplex target was normal, therefore the fluorescent substituents had no significant effect upon association kinetics. Moreover, the emission maxima of the fluoescein-$dA_{12}$ strand was 523 nm while the emission maxima of the rhodamine-$dT_{12}$ strand was 590 nm. Such a difference in emission maxima permits separate monitoring of the association kinetics of the two strands.

Strand displacement reactions are done, for example, at 10° C. in a 1 cm fluorescence cuvette. Reaction conditions are 100 mM NaCl, 10 mM Mg $Cl_2$ and 10 mM Tris-HCl, pH 7.0 with a reaction volume of 3 ml. Labeled duplex is allowed to equilibrate for at least 1 hr at 10° C. before addition of an excess of linear or circular oligonucleotide, e.g. a 40-fold excess to yield a final DNA concentration of about 0.01 μM. A Spex Flurolog F 111A fluorescence instrument with 5 mm slit widths is used to monitor the fluorescence emitted. An excitation wavelength of 450 nm and a monitored emission wavelength of 523 nm are used. Reactions are followed for at least 5 half-lives.

Addition of rhodamine-$dT_{12}$ to fluorescein-$dA_{12}$ can cause a decrease in fluorescein fluorescence and an increase in rhodamine fluorescence. Such effects are due to energy transfer between the fluorescent moieties (Cardullo et al.).

The association rate constant of the two fluorescently-labeled strands is determined by mixing the strands under pseudo-first order conditions and monitoring the rate of decrease in fluorescein emission.

An excess of unlabeled linear oligonucleotide (SEQ ID NO:19) or stem-loop oligonucleotide (SEQ ID NO:20) is added to the SEQ ID NO:18 duplex DNA to observe whether a fluorescently labeled strand is displaced from the duplex. An observed increase in fluorescein emission at a temperature significantly below the Tm of the duplex target is an indicator of duplex target strand dissociation.

Duplex target dissociation by the stem-loop oligonucleotide is considerably faster than is dissociation by the linear oligonucleotide. The first order rate constant for dissociation by a stem-loop oligonucleotide can be much faster than the rate constant for a linear oligonucleotide.

Moreover, while a duplex has a half-life for dissociation of 58 min in the presence of the linear oligonucleotide, the duplex can have a much shorter half-life in the presence of a stem-loop oligonucleotide.

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
CCTTTTTTTT CTCTCTTTTT TTTCC                                          25
```

( 2 ) INFORMATION FOR SEQ ID NO:2:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

```
TCGCCTTTTT TTTCTCTCTT TTTTTCCCG A                                    31
```

( 2 ) INFORMATION FOR SEQ ID NO:3:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
GCATCGCCTT TTTTTCTCT CTTTTTTTC CCGATGC                               37
```

( 2 ) INFORMATION FOR SEQ ID NO:4:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

```
GCAGCATCGC CTTTTTTTTC TCTCTTTTTT TTCCCGATGC TGC                      43
```

( 2 ) INFORMATION FOR SEQ ID NO:5:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

GCAGCAGCAT CGCCTTTTTT TTCTCTCTTT TTTTTCCCGA TGCTGCTGC    49

( 2 ) INFORMATION FOR SEQ ID NO:6:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

AAAAAAAA    8

( 2 ) INFORMATION FOR SEQ ID NO:7:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

TTTTTTTT    8

( 2 ) INFORMATION FOR SEQ ID NO:8:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

TCGCCTTTCT TTTCTCTCTT TTTTTCCCG A    31

( 2 ) INFORMATION FOR SEQ ID NO:9:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

GACTCTAGAA AAAAAAGACT CTAG    24

( 2 ) INFORMATION FOR SEQ ID NO:10:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

GCATCGACTT CTTTTCTTTC CACACCTTTC TTTTCTTCAC GATGC    45

( 2 ) INFORMATION FOR SEQ ID NO:11:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

T T C T T T T C T T   T C                                                                                    1 2

( 2 ) INFORMATION FOR SEQ ID NO:12:

( i ) SEQUENCE CHARACTERISTICS:
            ( A ) LENGTH: 12 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:12:

A A G A N A A G A A   A G                                                                                    1 2

( 2 ) INFORMATION FOR SEQ ID NO:13:

( i ) SEQUENCE CHARACTERISTICS:
            ( A ) LENGTH: 12 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:13:

A A G A A A A N A A   A G                                                                                    1 2

( 2 ) INFORMATION FOR SEQ ID NO:14:

( i ) SEQUENCE CHARACTERISTICS:
            ( A ) LENGTH: 12 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:14:

A A G A A T A G A A   A G                                                                                    1 2

( 2 ) INFORMATION FOR SEQ ID NO:15:

( i ) SEQUENCE CHARACTERISTICS:
            ( A ) LENGTH: 12 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:15:

A A G A A U A G A A   A G                                                                                    1 2

( 2 ) INFORMATION FOR SEQ ID NO:16:

( i ) SEQUENCE CHARACTERISTICS:
            ( A ) LENGTH: 45 base pairs
            ( B ) TYPE: nucleic acid
            ( C ) STRANDEDNESS: single
            ( D ) TOPOLOGY: linear ( i i ) MOLECULE TYPE: DNA (genomic)

( x i ) SEQUENCE DESCRIPTION: SEQ ID NO:16:

GCATCGACTT CTTCTCTTTC CACACCTTTC TATTCTTCAC GATGC    45

( 2 ) INFORMATION FOR SEQ ID NO:17:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

CTTTCTATTC TT    12

( 2 ) INFORMATION FOR SEQ ID NO:18:

( i ) SEQUENCE CHARACTERISTICS:
        ( A ) LENGTH: 12 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:18:

AAAAAAAAAA AA    12

( 2 ) INFORMATION FOR SEQ ID NO:19:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

TTTTTTTTTT TT    12

( 2 ) INFORMATION FOR SEQ ID NO:20:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

GCATCGACTT TTTTTTTTTT CACACTTTTT TTTTTTCAC GATGC    45

( 2 ) INFORMATION FOR SEQ ID NO:21:

( i ) SEQUENCE CHARACTERISTICS:
        ( A ) LENGTH: 188 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:21:

-continued

| TAAGCTTGAT | ATTCTCCCCA | GATGTAGTGA | AAGCAGGTAG | ATTGCCTTGC | CTGGACTTGC | 60 |
| CTGGCCTTGC | CTTTTCTTTC | TTTCTTTCTT | TCTTTATTAC | TTTCTCTTTT | TCTTCTTCTT | 120 |
| CTTCTTCTTC | TTCTTCTTCT | TCTTCTTCTT | CTTCTTCTTC | TTCTTCTTCT | TTTTTTTTG | 180 |
| AGACAGAG | | | | | | 188 |

What is claimed:

1. A stem-loop oligonucleotide comprising a double-stranded stem domain of at least about 2 base pairs and a single-stranded loop domain comprising at least one parallel binding (P) domain separated by at least about 3 nucleotides from a corresponding anti-parallel binding (AP) domain;
   wherein each P and corresponding AP domain simultaneously and detectably binds to one strand of a defined nucleic acid target;
   and wherein said P domain binds in a parallel manner to said target and said corresponding AP domain binds in an anti-parallel manner to said target.

2. The oligonucleotide of claim 1 wherein said target, said P domain and said AP domain independently comprise from about 2 to about 200 nucleotides.

3. The oligonucleotide of claim 2 wherein said target, said P domain and said AP domain independently comprise from about 6 to about 36 nucleotides.

4. The oligonucleotide of claim 1 wherein each P domain is separated from a corresponding AP domain by about 3 to about 2000 nucleotides.

5. The oligonucleotide of claim 4 wherein each P domain is separated from a corresponding AP domain by about 4 to about 8 nucleotides.

6. The oligonucleotide of claim 1 wherein said target is single-stranded or double-stranded.

7. The oligonucleotide of claim 1 wherein said target is RNA or DNA.

8. The oligonucleotide of claim 1 wherein said target consists of a domain located within the sequence of a nucleic acid template.

9. The oligonucleotide of claim 1 wherein said P domain and said AP domain bind to said target in a staggered binding arrangement resulting in a target:stem-loop oligonucleotide complex which is partially two stranded and partially three-stranded and wherein said two stranded portion of said complex comprises at least one of a P:target duplex, without bound AP nucleotides, or an AP:target duplex, without bound P nucleotides.

10. The oligonucleotide of claim 1 wherein said P domain or said AP domain have less than 100% complementarity to said target.

11. The oligonucleotide of claim 10 wherein said P domain or said AP domain have about 30% to about 40% complementarity to said target.

12. The oligonucleotide of claim 1 wherein said oligonucleotide is DNA or RNA.

13. The oligonucleotide of claim 1 wherein said oligonucleotide is taken up in a cell.

14. The oligonucleotide of claim 1 wherein said oligonucleotide is a conjugated oligonucleotide further comprising at least one of a cellular receptor, cholesterol group, an aryl group, a steroid group or a polycation.

15. The oligonucleotide of claim 1 wherein said P and AP domains are separated by a non-nucleotide spacer.

16. The oligonucleotide of claim 15 wherein said non-nucleotide spacer is polyethylene glycol.

17. The oligonucleotide of claim 16 wherein said polyethylene glycol is pentaethylene glycol, hexaethylene glycol or heptaethylene glycol.

18. The oligonucleotide of claim 1 wherein said oligonucleotide further comprises at least one methylphosphonate, phosphorothioate, phosphorodithioate, phosphotriester, siloxane, carbonate, acetamidate, thioether or phosphorus-boron linkage.

19. The oligonucleotide of claim 1 wherein said oligonucleotide is a conjugated oligonucleotide further comprising a reporter molecule.

20. The oligonucleotide of claim 1 wherein two nucleic acid strands of said stem domain are covalently cross-linked.

21. A kit for the isolation, detection or diagnosis of a target nucleic acid, comprising:
   at least one first container providing a stem-loop oligonucleotide of claim 1 wherein at least one P domain and corresponding AP domain of said oligonucleotide can selectively bind to said target nucleic acid.

22. The kit of claim 21 wherein said target is poly $(A)^+$ mRNA.

23. An expression vector comprising a sequence encoding the oligonucleotide of claim 1 operably linked to a segment of said vector which effects expression of an RNA copy of said oligonucleotide.

24. The expression vector of claim 23 wherein said vector is a eukaryotic expression vector.

25. A complex formed between the oligonucleotide of claim 1 and a target.

26. The oligonucleotides of claim 1 wherein said oligonucleotide comprises a first pair of corresponding P and AP binding domains and a second pair of corresponding P and AP binding domains;
   wherein the corresponding P and AP binding domains of said first pair each constitute at least part of a spacer separating the P binding domain and the AP binding domain of said second pair, when said second pair binds to a second target;
   wherein the corresponding P and AP binding domains of said second pair each constitute at least part of a spacer separating the P binding domain and the AP binding domain of said first pair, when said first pair binds to a first target.

27. The oligonucleotide of claim 26 wherein said first pair of P and AP domains each comprise 2–20 cytosines while said second pair of P and AP binding domains each comprise no more than 1 cytosine.

* * * * *

UNITED STATES PATENT AND TRADEMARK OFFICE
CERTIFICATE OF CORRECTION

PATENT NO. : 5,808,036
DATED : September 15, 1998
INVENTOR(S) : Eric T. Kool

It is certified that error appears in the above-identified patent and that said Letters Patent is hereby corrected as shown below:

Column 15,
Line 35, "Retrovirol" should not begin a new paragraph.

Column 17,
Line 64, "The" should not begin a new paragraph.

Column 18,
Line 9, "For" should not begin a new paragraph.
Line 14, "In" should not begin a new paragraph.

Column 19,
Line 11, "These" should not begin a new paragraph.

Column 21,
Line 37, "These" should not begin a new paragraph.

Signed and Sealed this

Eighteenth Day of December, 2001

Attest:

JAMES E. ROGAN
Director of the United States Patent and Trademark Office

Attesting Officer